US008848181B1

United States Patent
Meeks et al.

(10) Patent No.: US 8,848,181 B1
(45) Date of Patent: Sep. 30, 2014

(54) MULTI-SURFACE SCATTERED RADIATION DIFFERENTIATION

(71) Applicants: Steven W. Meeks, Palo Alto, CA (US); Rusmin Kudinar, Fremont, CA (US); Hung P. Nguyen, Santa Clara, CA (US)

(72) Inventors: Steven W. Meeks, Palo Alto, CA (US); Rusmin Kudinar, Fremont, CA (US); Hung P. Nguyen, Santa Clara, CA (US)

(73) Assignee: Zeta Instruments, Inc., San Jose, CA (US)

( * ) Notice: Subject to any disclaimer, the term of this patent is extended or adjusted under 35 U.S.C. 154(b) by 25 days.

(21) Appl. No.: 13/861,383

(22) Filed: Apr. 12, 2013

(51) Int. Cl.
G01N 21/00 (2006.01)
G01N 21/958 (2006.01)

(52) U.S. Cl.
CPC .................................. *G01N 21/958* (2013.01)
USPC ....................................................... 356/239.7

(58) Field of Classification Search
CPC ..................................................... G01N 21/598
USPC ....................................................... 356/239.7
See application file for complete search history.

(56) References Cited

U.S. PATENT DOCUMENTS

| 4,626,101 | A | 12/1986 | Ogawa et al. |
| 6,069,690 | A | 5/2000 | Xu et al. |
| 6,624,884 | B1 | 9/2003 | Imaino et al. |
| 6,686,602 | B2 | 2/2004 | Some |
| 6,704,435 | B1 | 3/2004 | Imaino et al. |
| 6,791,099 | B2 | 9/2004 | Some et al. |
| 7,907,269 | B2 | 3/2011 | Meeks |
| 2004/0186351 | A1* | 9/2004 | Imaizumi et al. ............. 600/160 |
| 2005/0046848 | A1* | 3/2005 | Cromwell et al. ............ 356/417 |
| 2009/0250628 | A1 | 10/2009 | Mano |
| 2012/0049085 | A1 | 3/2012 | Sappey et al. |

OTHER PUBLICATIONS

Zhiqiang Li, Thomas Ryan, Proc. of SPIE vol. 7231. Light-Emitting Diodes: Materials, Devices, and Applications for Solid State Lighting XIII, Edited by Klaus P. Streubel, Heonsu Jeon, Li-Wei Tu, Proc. of SPIE vol. 7231, 72310P, 2009.

* cited by examiner

*Primary Examiner* — Tarifur Chowdhury
*Assistant Examiner* — MD Rahman
(74) *Attorney, Agent, or Firm* — Imperium Patent Works; Mark D. Marrello

(57) ABSTRACT

An optical inspector includes a radiating source, a time varying beam reflector, a telecentric scan lens, a first and second waveplate, a polarizing beam splitter, a first detector, a focusing lens, a blocker, and a second detector. The radiating source irradiates the first waveplate generating circularly polarized source beam that irradiates a first position of on the time varying beam reflector with a source beam. The time varying beam reflector directs the source beam to the telecentric scan lens, which in turn directs the source beam to a sample. Reflected radiation from a sample is directed to the second waveplate generating linearly polarized beam that irradiates the polarizing beam splitter which directs a portion of the reflected radiation to the first detector. Scattered radiation from the sample is directed by the focusing lens to the second detector. Contemporaneous measurements by the first and second detectors are compared to differentiate.

19 Claims, 19 Drawing Sheets

TOP VIEW
OPTICAL INSPECTOR

TRANSPARENT WAFER
(CROSS-SECTIONAL VIEW)

OPTICAL INSPECTOR
TOP VIEW

OPTICAL INSPECTOR
SIDE VIEW

OPTICAL INSPECTOR

INTERNAL VS EXTERNAL REFLECTION FROM TRANSPARENT SAMPLE

BOTTOM SURFACE AND TOP SURFACE REFLECTIONS DO NOT MIX. EACH DETECTOR RECEIVES REFLECTION FROM ONLY ONE OF THE SURFACES.

SEPARATION OF TOP AND BOTTOM SURFACE REFLECTION

OPTICAL INSPECTOR WITHOUT BLOCKER OF STAGE SCATTERED RADIATION

EXPANDED VIEW - OPTICAL INSPECTOR WITHOUT BLOCKER OF STAGE SCATTERED RADIATION

EXPANDED VIEW - OPTICAL INSPECTOR WITH BLOCKER OF STAGE SCATTERED RADIATION

EXPANDED VIEW - OPTICAL INSPECTOR WITH BLOCKER OF STAGE SCATTERED RADIATION

OPTICAL INSPECTOR WITH BLOCKER OF STAGE SCATTERED RADIATION

OPTICAL INSPECTOR WITH BLOCKER OF STAGE SCATTERED RADIATION

SAMPLE DEFECT MAPPING

INTENSITY MAPPING OF SCATTERED RADIATION AND SPECULAR REFLECTION

T1 = SCATTERED LIGHT THRESHOLD INTENTSITY VALUE.
T2 = TOP SURFACE SPECULAR REFLECTION THRESHOLD INTENSITY VALUE.

INTENSITY VS SCAN LINE POSITION

| X POSITION | Y POSITION | SR > T1? | SP < T2? | SURFACE SOURCE OF SCATTERED RADIATION |
|---|---|---|---|---|
| X1 | Y1 | TRUE | TRUE | TOP SURFACE SCATTERED RADIATION |
| X2 | Y1 | TRUE | FALSE | BOTTOM SURFACE SCATTERED RADIATION |
| X3 | Y1 | TRUE | TRUE | TOP SURFACE SCATTERED RADIATION |
| X1 | Y2 | TRUE | FALSE | BOTTOM SURFACE SCATTERED RADIATION |
| X2 | Y2 | TRUE | TRUE | TOP SURFACE SCATTERED RADIATION |
| X3 | Y2 | TRUE | FALSE | BOTTOM SURFACE SCATTERED RADIATION |

SR = SCATTERED RADIATION INTESNISTY.
SP = SPECULAR REFLECTION INENTISTY FROM TOP SURFACE OF THE SAMPLE.
T1 = SCATTERED RADIATION THRESHOLD INTENTSITY VALUE.
T2 = TOP SURFACE SPECULAR REFLECTION THRESHOLD INTENSITY VALUE.

TOP SURFACE SPECULAR REFLECTION SCATTERED RADIATION
DISTINGUISHING LOGIC TABLE

FIG. 17

| X POSITION | Y POSITION | SR > T1? | SP < T3? | SURFACE SOURCE OF SCATTERED RADIATION |
|---|---|---|---|---|
| X1 | Y1 | TRUE | TRUE | BOTTOM SURFACE SCATTERED RADIATION |
| X2 | Y1 | TRUE | FALSE | TOP SURFACE SCATTERED RADIATION |
| X3 | Y1 | TRUE | TRUE | BOTTOM SURFACE SCATTERED RADIATION |
| X1 | Y2 | TRUE | FALSE | TOP SURFACE SCATTERED RADIATION |
| X2 | Y2 | TRUE | TRUE | BOTTOM SURFACE SCATTERED RADIATION |
| X3 | Y2 | TRUE | FALSE | TOP SURFACE SCATTERED RADIATION |

SR = SCATTERED RADIATION INTESNISTY.
SP = SPECULAR REFLECTION INENTISTY FROM BOTTOM SURFACE OF THE SAMPLE.
T1 = SCATTERED RADIATION THRESHOLD INTENTSITY VALUE.
T3 = BOTTOM SURFACE SPECULAR REFLECTION THRESHOLD INTENSITY VALUE.

BOTTOM SURFACE SPECULAR REFLECTION SCATTERED RADIATION
DISTINGUISHING LOGIC TABLE

FIG. 18

SEPARATION OF TOP VS BOTTOM SURFACE SCATTERED RADIATION

OPTICAL INSPECTION FLOWCHART

OPTICAL INSPECTION FLOWCHART

MULTI-SURFACE SCATTERED RADIATION DIFFERENTIATION

TECHNICAL FIELD

The described embodiments relate generally to detecting defects and more particularly to detecting defects in a transparent wafer.

BACKGROUND INFORMATION

Light Emitting Diodes (LEDs) are typically produced by an epitaxial deposition of alloys of gallium nitride (GaN) on a transparent wafer substrate such as a sapphire. Many different types of defects may appear on either the substrate or the epitaxial layer. Some of these defects may be cracks in the sapphire which can then appear in the GaN layer, growth defects in GaN layer, pits, particles and stains from contaminates. In many cases, LED manufacturers will deposit GaN layers on patterned sapphire substrates (PSS). PSS serves to improve the light extraction efficiency by reducing the amount of light which is guided by total internal reflection. Manufacturers also desire to detect defects in the PSS since this will result in additional GaN growth defects or reduced light extraction efficiency. Similarly, defects in other transparent wafers will also result in degraded performance of the resulting device.

The inspection of transparent substrates is complicated by the difficulty of separating the scattered light reflected from the top and bottom surfaces. A diagram of a transparent substrate is shown in FIG. 1. Illustrated in FIG. 1 is a 1 mm thick glass wafer (sample 1). It is desired to inspect the top surface of the glass wafer for defects and to exclude the scattered light signal from the bottom surface of the glass wafer. In the prior art, Meeks (U.S. Pat. No. 7,907,269) describes a method to separate top and bottom surface scattered light. Meeks teaches the use of either an oblique or normal laser wherein bottom surface scattered light is separated by means of a beam block with a pinhole.

SUMMARY

A surface optical inspector directs a source beam onto a surface of a sample and in response measures various types of radiation from the sample. The types of radiation include specular reflection, near specular scattered radiation, and scattered radiation. The measured information is processed to determine the total reflectivity of the sample, the surface slope of the sample, scattered radiation intensity from the sample, and near specular scattered radiation intensity from the sample. These measurements are in turn utilized to determine whether defects are present in the sample.

In a first novel aspect, the surface optical inspector includes a time varying beam reflector, a radiating source that irradiates a first position on the time varying beam reflector with source radiation, a telecentric scan lens that directs the source radiation from the time varying beam reflector onto a sample, a polarizing beam splitter that receives reflected radiation from the sample, and a first detector that receives a first portion of the reflected radiation from the polarizing beam splitter. The optical inspector may also include a second detector that receives a second portion of the reflected radiation. A first and second waveplate may also be included in the optical inspector. The second portion of the reflected radiation is not reflected by the polarizing beam splitter.

In a second novel aspect, the surface optical inspector includes a time varying beam reflector, a radiating source that irradiates a first position on the time varying beam reflector with source radiation, a telecentric scan lens that directs the source radiation from the time varying beam reflector onto a sample, a polarizing beam splitter that receives reflected radiation from the sample, a first detector that receives a first portion of the reflected radiation from the polarizing beam splitter, and a third detector that receives a third portion of the reflected radiation from the polarizing beam splitter. The third portion of the reflected radiation includes near specular scattered radiation.

In a third novel aspect, the surface optical inspector includes a radiating source that irradiates a first position of a time varying beam reflector, a telecentric scan lens that directs the radiation reflected by the time varying beam reflector onto a sample, a focusing lens that receives scattered radiation from the sample, a blocker that redirects scattered radiation from the stage away from the focusing lens, and a detector located near the focal plane of the focusing lens. Scattered radiation from the sample is not redirected by the blocker.

In a fourth novel aspect, the surface optical inspector includes a radiating source that irradiates a first position of a time varying beam reflector, a telecentric scan lens that directs the radiation reflected by the time varying beam reflector onto a sample, a beam splitter that receives specular reflected radiation from the transparent sample, a focusing lens that receives scattered radiation from the sample, a blocker that redirects scattered radiation from the stage away from the focusing lens, a first detector that receives a first portion of the specular reflected radiation from the beam splitter, and a second detector located near the focal plane of the focusing lens. Scattered radiation from the sample is not redirected by the blocker. The surface optical inspector may also include a first and second waveplate, memory, and a processor that samples the output of the first and second detector.

In a fifth novel aspect, the time varying beam reflector is a rotating polygon, the sample is a wafer or disc, the scattered radiation includes a top surface scattered radiation generated from the top surface of the sample and a bottom surface scattered radiation generated from the bottom surface of the sample, the first lens is a camera lens, the blocker is opaque and blocks the scattered radiation from the stage, the radiating source is a laser, the first detector is a photodiode bi-cell, and the second detector is a photomultiplier tube detector.

Further details and embodiments and techniques are described in the detailed description below. This summary does not purport to define the invention. The invention is defined by the claims.

BRIEF DESCRIPTION OF THE DRAWINGS

The accompanying drawings, where like numerals indicate like components, illustrate embodiments of the invention.

FIG. 17 is a table of scattered radiation separation logic based on top surface specular reflection.

FIG. 18 is a table of scattered radiation separation logic based on bottom surface specular reflection.

DETAILED DESCRIPTION

Reference will now be made in detail to background examples and some embodiments of the invention, examples of which are illustrated in the accompanying drawings. In the description and claims below, relational terms such as "top", "down", "upper", "lower", "top", "bottom", "left" and "right" may be used to describe relative orientations between different parts of a structure being described, and it is to be understood that the overall structure being described can actually be oriented in any way in three-dimensional space.

Figure 1:
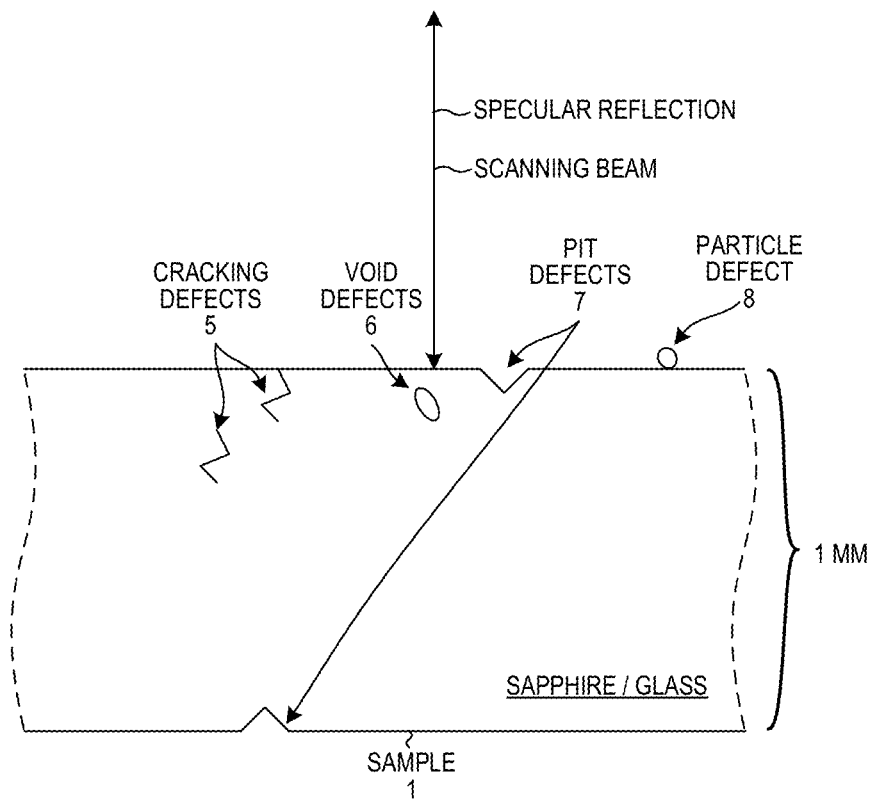
FIG. 1 is a cross-sectional diagram of a transparent wafer.

FIG. 1 is a cross-sectional diagram of a transparent wafer (i.e. a sample 1). During the fabrication of the transparent wafer, unwanted defects can be produced. These unwanted defects include cracking defects 5, void defects 6, pit defects 7, and particle defects 8. These defects may occur in varies locations within the transparent wafer. These defects result in undesirable results such as reduced operating life of the resulting LED device, non-functionality of the resulting LED device, and degraded performance (light efficiency) of the resulting LED device. It is valuable to a LED manufacturer to detect these defects before additional resources are spent developing a product that will not function properly due to wafer level defects.

It is noted herein, the example of a GaN LED is used for exemplary use only. This disclosure is not limited to the detection of defects in a GaN LED. Further, the example of a sapphire substrate and a glass wafer are used for exemplary use only. This disclosure is not limited to the detection of defects in sapphire or glass wafers. Rather, this disclosure is applicable to all transparent or opaque wafers or discs regardless of the specific material constituting the wafer/disc or the end device to be manufactured with the developed wafer/disc.

Figure 2:
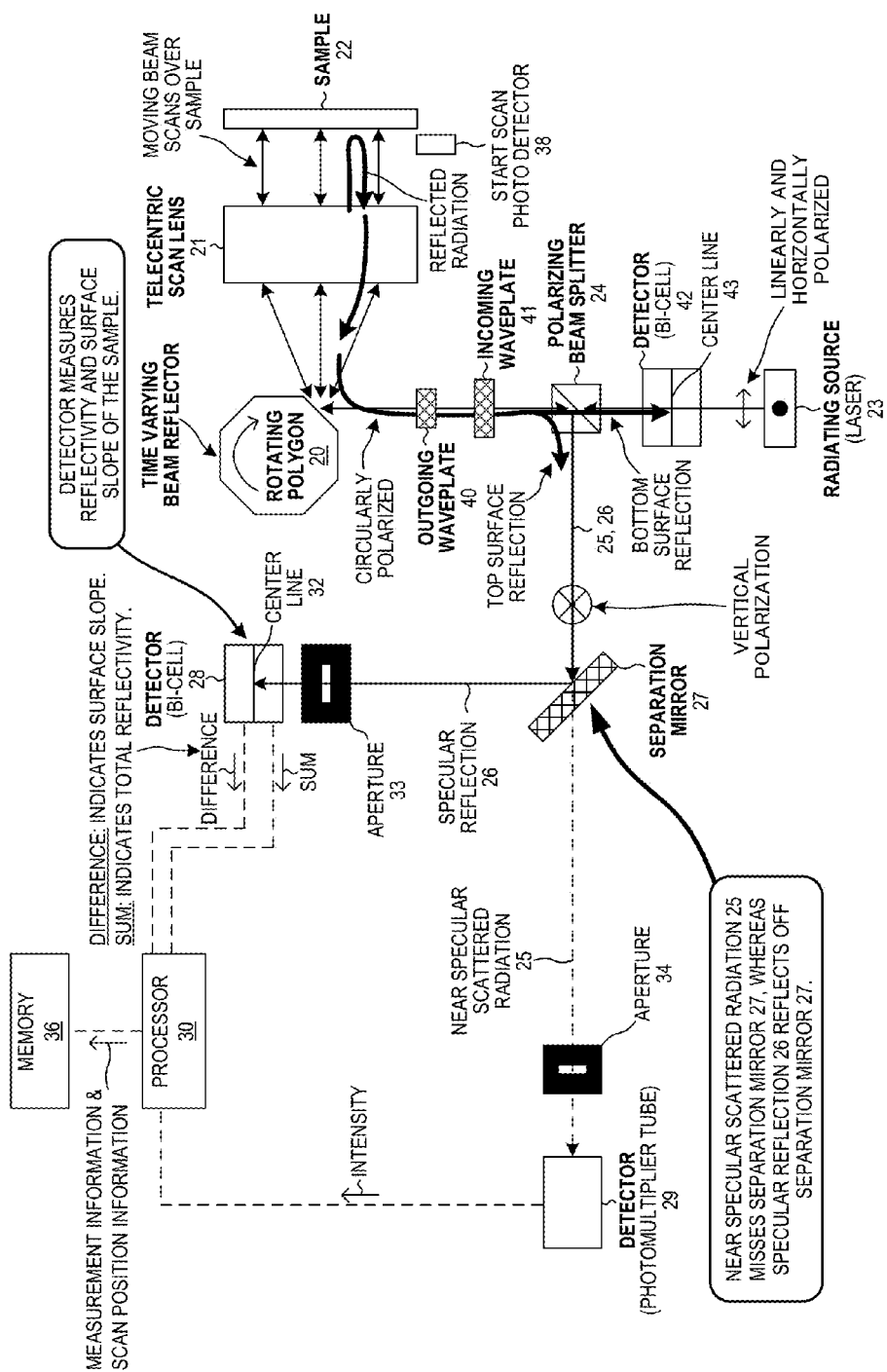
FIG. 2 is a top-view diagram of an optical inspector.

FIG. 2 is a top view diagram of an optical inspector. The optical inspector includes a time varying beam reflector (rotating polygon 20), a telecentric scan lens 21, a radiating source 23, a polarizing beam splitter 24, an outgoing waveplate 40, an incoming waveplate 41, a separation mirror 27, a bi-cell photo detector 28, and a photomultiplier tube detector 29. It is noted herein, the use of rotating polygon is exemplary. Any time varying beam reflector, such as a resonant galvanometer, a rotating double sided mirror, or acousto-optic beam deflector can be utilized as well.

The radiating source 23 irradiates outgoing waveplate 40 with a source beam. In one example, the radiating source 23 is a laser. Outgoing waveplate 40 converts the linearly polarized source beam to a circularly polarized source beam. The circularly polarized source beam is directed by the rotating polygon 20 to a first location on the telecentric scan lens 21. The angle at which the source beam approaches the telecentric scan lens 21 depends upon the angle of rotation of the rotating polygon 20 when the source beam contacts the rotating polygon 20. However, regardless of the angle at which the source beam approaches the telecentric scan lens 21, the telecentric scan lens 21 directs the source beam to a sample 22 at an angle that is substantially normal to the surface of the sample 22. In one example, the sample is the transparent wafer (sample 1) shown in FIG. 1.

The source beam directed, at a substantially normal angle, to the sample 22 generates a reflection of the source beam. A first portion of the reflected source beam is specular reflection. A second portion of the reflected source beam is near specular scattered radiation. Specular reflection is the mirror-like reflection of light from a surface, in which light from a single incoming direction is reflected into a single outgoing direction (in adherence with the law of reflection). Near specular scattered radiation is light which is scattered (or deflected) by defects in a region which is just outside the profile of the specular beam. Measuring both the specular reflection and the near specular scattered radiation allows the detection of defects which may not be visible in the specular reflection alone.

The reflected radiation, including specular reflection 26 and the near specular scattered radiation 25, is reflected back to the telecentric scan lens 21. The telecentric scan lens 21 directs the specular reflection 26 and the near specular scattered radiation 25 to the rotating polygon 20. The rotating polygon 20 directs the specular reflection 26 and near specular scattered radiation 25 back toward the radiating source 23. At this point, separating the source beam from the reflected light would be impractical if both the source beam and the reflected beams were traveling in the same space. To avoid this problematic situation, the radiating source 23 is placed at a location at an offset from the central axis 31 of the telecentric scan lens 21. The central axis 31 is illustrated in the side view portion of FIG. 3. As shown in the side view diagram of FIG. 3, when the radiating source 23 is offset from the central axis 31, the beam approaches the sample 22 at a small non-normal angle, thus resulting in the reflected beam reaching the telecentric scan lens 21 at a position symmetrically opposite the central axis 31. This directs the reflected radiation away from the radiating source 23 without altering the source beam radiating from the radiating source 23.

Figure 5:
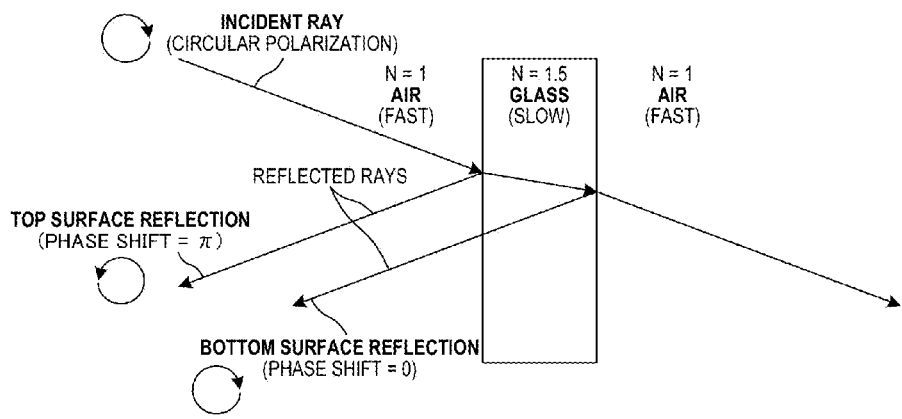
FIG. 5 is a diagram of internal versus external reflection from a transparent sample.

The reflected radiation originating from the top surface of the sample is different from the reflected radiation originating from the bottom surface of the sample. The difference in reflected radiation is illustrated in FIG. 5. The reflected radiation originating from the top surface of the sample has a phase shift of approximately one hundred and eighty degrees (or $\pi$ radians). Alternatively, the reflected radiation originating from the bottom surface of the sample has a phase shift of approximately zero degrees (or zero radians).

Figure 6:
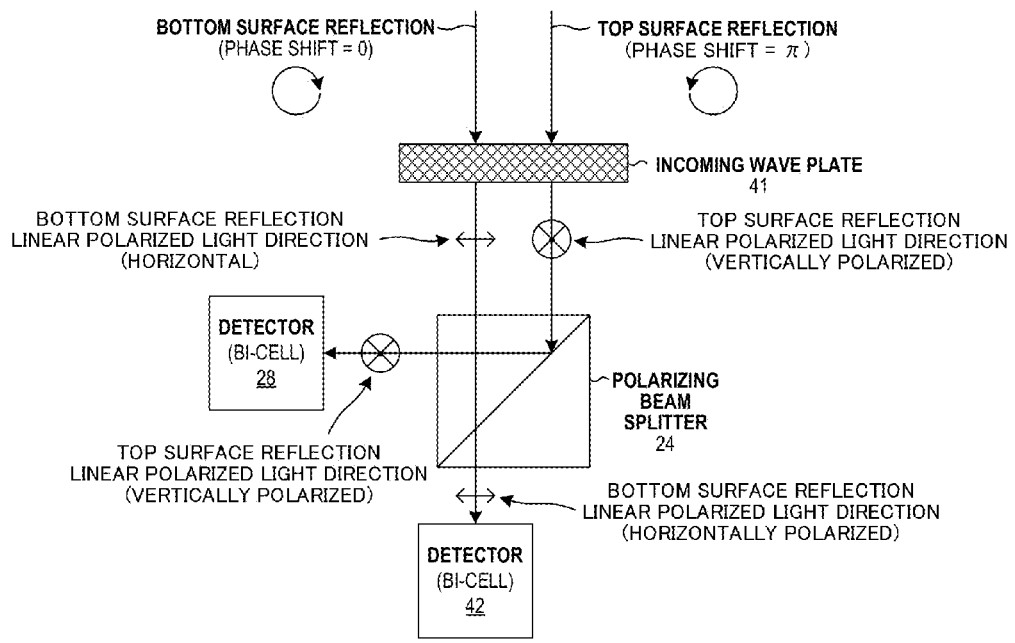
FIG. 6 is a diagram illustrating the separation of top and bottom surface reflection by use of a polarizing beam splitter.

The reflected radiation originating from both the top and bottom surface of the sample is directed by rotating polygon 20 to incoming waveplate 41. As illustrated in FIG. 6, incoming waveplate 41 converts circularly polarized reflected radiation to linearly polarized radiation. Incoming waveplate 41 converts the reflected radiation originating from the top surface of the sample to vertically polarized radiation. Simultaneously, incoming waveplate 41 converts the reflected radiation originating from the bottom surface of the sample to horizontally polarized radiation. The linearly polarized reflected radiation is then directed to polarizing beam splitter 24. As shown in FIG. 2 and FIG. 6, the polarizing beam splitter 24 redirects the vertically polarized reflected radiation originating from the top surface of the sample; however, the polarizing beam splitter 24 does not redirect the horizontally polarized reflected radiation originating from the bottom surface of the sample. Thus, the specular reflection 26 and the near specular scattered radiation 25 (originating from the top surface of the sample) are directed by polarizing beam splitter 24 toward separation mirror 27. Separation mirror 27 directs the specular reflection 26 to the bi-cell photo detector 28. Simultaneously, near specular scattered radiation 25 travels above and/or below separation mirror 27 toward photomultiplier tube detector 29. The reflected radiation from the bottom surface of the sample passes through the polarizing beam splitter 24 and travels to bi-cell photo detector 42. This solution allows for the separation of reflected radiation from the top surface of the sample from reflected radiation from the bottom surface of the sample.

Figure 3:
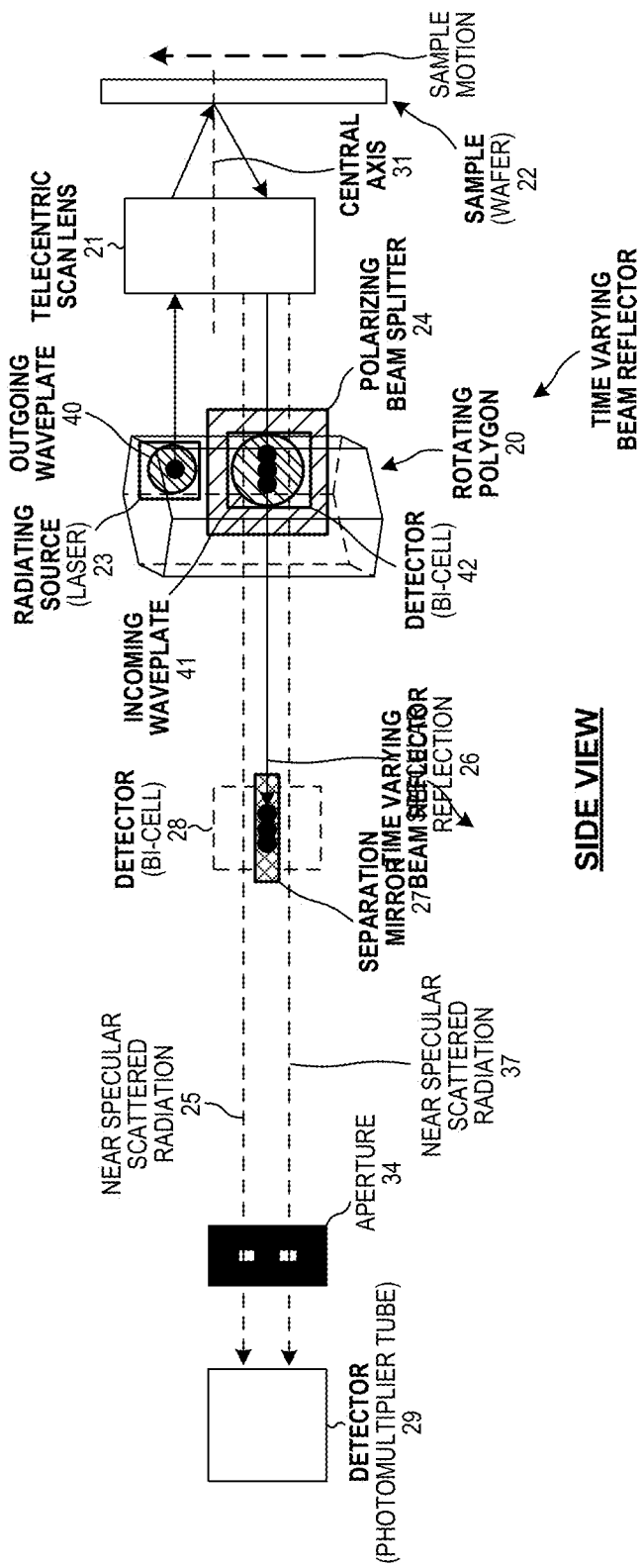
FIG. 3 is a side-view diagram of a first example of an optical inspector.

In one example, as shown in FIG. 3, separation mirror 27 is placed at the exact location of the specular reflection 26 beam and separation mirror 27 has a height that is approximately equal to the beam width of the specular reflection beam. As such, a portion of the reflected beam that travels at a height greater than the height of the top edge of separation mirror 27 continues to photomultiplier tube detector 29. Likewise, any portion of the reflected beam that travels at a height less than the height of the bottom edge of separation mirror 27 continues to the photomultiplier tube detector 29. These portions of the reflected beam that travel above and below separation mirror 27 are labeled near specular scattered radiation 25, 37 in FIG. 3.

Figure 4:
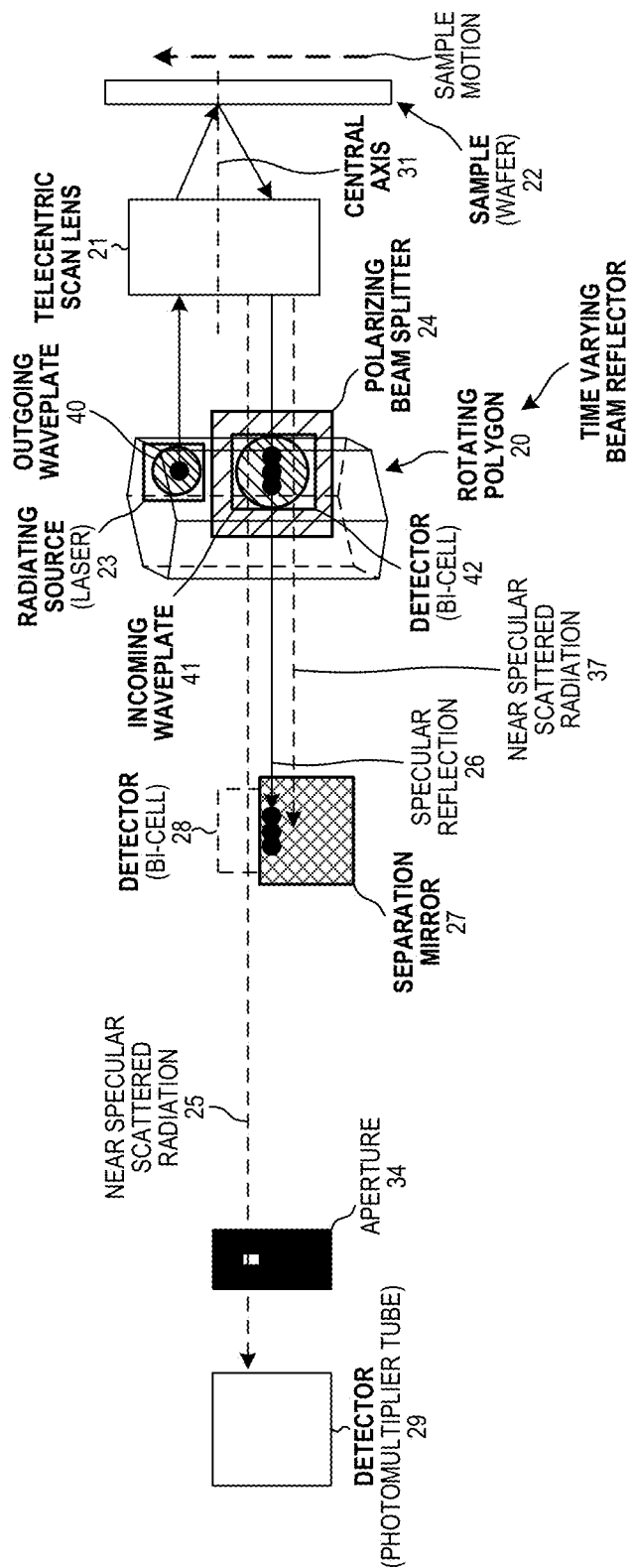
FIG. 4 is a side-view diagram of a second example of an optical inspector.

In a second example, as shown in FIG. 4, separation mirror 27 is placed at the location of the specular reflection 26, separation mirror 27 has a height that is greater than the beam width of the specular reflection beam, and the top edge of separation mirror 27 is aligned to the top edge of specular reflection beam. As such, a portion of the reflected beam that travels at a height greater than the height of the top edge of separation mirror 27 continues to the photomultiplier tube 29. Alternatively, any portion of the reflected beam that travels at a height less than the height of the bottom edge of specular reflection beam is directed toward bi-cell detector 28. The portion of the reflected beam that travels above separation mirror 27 is near specular scattered radiation 25. The portion of the reflected beam that is reflected by separation mirror 27 is predominantly near specular scattered radiation 37.

In another example, an aperture 33 is included between separation mirror 27 and bi-cell detector 28. Aperture 33 serves to block any near specular scattered radiation directed toward bi-cell detector 28 from separation mirror 27. In an alternative example, aperture 34 is included between mirror 27 and photomultiplier tube detector 29. Aperture 34 serves to block any non-near specular scattered radiation directed toward photomultiplier tube detector 29 from mirror 27.

The bi-cell detector 28 is located such that the specular reflection 26 should irradiate the bi-cell detector 28 on the center line 32 (as shown in FIGS. 2, 3 and 4) between the two photodiodes included in the bi-cell detector 28. In the event that the surface slope (the "micro-waviness") of the sample is not normal to the source beam, the resulting specular reflection 26 will deviate from the center line 32. A deviation from the center line 32 will cause a greater amount of the specular reflection 26 to irradiate one of the two photodiodes in the bi-cell detector 28. In response, the bi-cell detector 28 will output an increased difference value indicating a change in the slope of the sample 22 surface. A negative difference value indicates a slope varying in a first direction. A positive difference value indicates a slope varying in a second direction. The slope measured is the surface slope of the sample 22 in direction perpendicular to the optical scan line. Regardless of the deviation of the specular reflection 26 from the center line 32, the bi-cell detector 28 will output a sum value indicating the reflectivity of the sample 22.

In another example, a processor 30 is also included in the top surface optical inspector shown in FIG. 2. The processor 30 receives the intensity output signal from the photomultiplier tube detector 29, a difference output signal from bi-cell detector 28, a difference output signal from bi-cell detector 42, a sum output signal from bi-cell detector 28, and a sum output signal from bi-cell detector 42. In response, processor 30 determines whether defects are present at the scan location on the sample 22.

The processor may also communicate with a motor controlling rotating polygon 20. The processor may increase or decrease the rate of rotation of the rotating polygon 20. For example, when switching from using a high-bandwidth detector to a low-bandwidth detector, it may be required that the rate of rotation of the rotating polygon 20 be decreased. Alternatively, when switching from using a low-bandwidth detector to a high-bandwidth detector, it may be necessary to increase the rate of rotation of the rotating polygon 20.

In another example, memory 36 is included in the top surface optical inspector shown in FIG. 2. Memory 36 stores information output by processor 30. (i.e. defect information, or defect indicator information). Memory 36 also stores location information indicating the location on the sample which was scanned to measure the defect information or defect indicator information. Defect information is a status as to whether the scanned location on the sample contains a defect or not. Defect indicator information includes various measurements from the scanned location on the sample (i.e. surface slope, total reflectivity, intensity of scattered radiation, intensity of near specular scattered radiation).

The amount of near specular scattered light which is collected is limited by the size of the polygon mirror facets and the size of the polarizing beam splitter 24. The near specular scattered radiation passes above the separation mirror 27 and is incident on the photomultiplier tube (PMT) detector. The PMT measures the intensity of the near specular scattered light. Localized defects will appear as variations (increases or decreases) in the near specular scattered light signal.

In one example, the scan of the sample is done with the polygon rotating at a high speed and the data sampling of the bi-cell detector is run at approximately 16 MHz with the radiating source running at full intensity. Since the rotating polygon can rotate at high speeds, an entire 100 mm diameter sample can be measured in about ten seconds.

In another example, the rotating polygon begins to spin upon power up of the device and continues to spin until the entire device is powered off. The constant spinning of the rotating polygon during operation is beneficial in that spin-up and spin-down delay time is eliminated during regular operation. As shown in FIGS. 3 and 4, the sample is moved in the direction shown by a precision stage (not shown) to make a map of the entire sample surface. In one embodiment, shown in FIG. 2, the optical inspector includes a start of scan photodetector 38 which is placed at the edge of the scan line and serves to trigger the acquisition of data sampling when the scanned beam passes over the detector 38.

This above process is repeated as the sample 22 is moved underneath the optical inspector. A precision stage controller directs the movement of the sample 22 during the inspection process. In one example, the processor 30 outputs defect inspection data which is logged along with the sample scan location. The number and location of defects on the sample will determine the disposition of the sample. In one example, depending upon the location and type of defect, some portions of the sample may be useful and others portions of the sample may be discarded. In another example, if the sample has many defects then the entire sample may be discarded.

It is noted herein, that the bi-cell detectors 28 and 42 are of exemplary use in this disclosure. One skilled in the art will readily realize that the bi-cell detectors 28 and 42 may be replaced with various multi-cell detectors to achieve the utility of the present invention.

It is noted herein, that the use of a photomultiplier tube detector 29 is of exemplary use in this disclosure. One skilled in the art will readily realize that the photomultiplier tube detector 29 may be replaced with other light sensing detectors such as a silicon photodetector to achieve the utility of the present invention.

Prior art, Meeks (U.S. Pat. No. 7,907,269) uses a pinhole and a beam block to separate top and bottom surface scatter. The difficulty with the prior art lies in the difficulty in aligning the pinhole. Therefore, there is a need for a new apparatus, method, and means for separating top surface and bottom surface scattered radiation from transparent substrates without the use of a pinhole.

Figure 7:
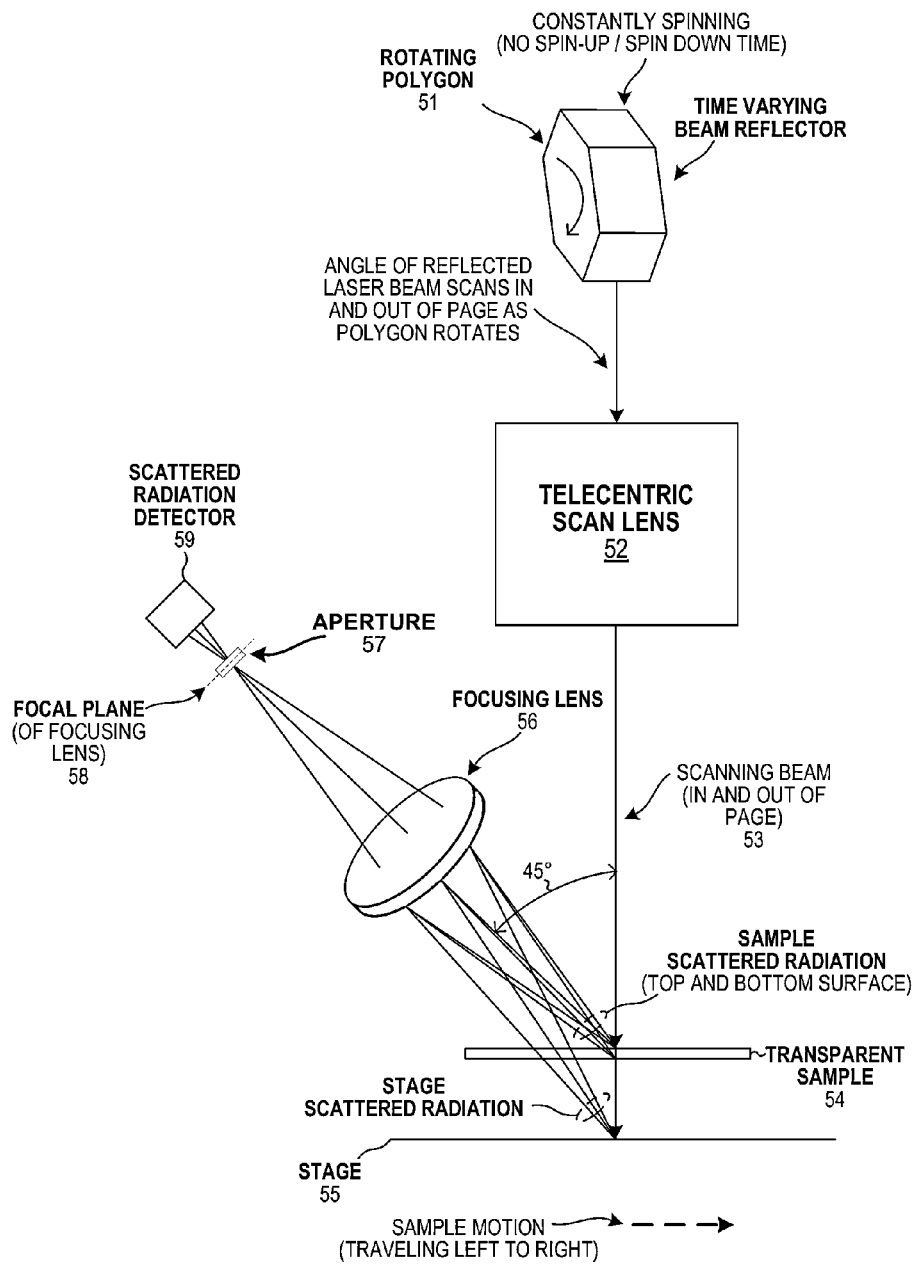
FIG. 7 is a diagram of an optical inspector without a blocker.

FIG. 7 is a diagram of an optical inspector. The optical inspector includes a rotating polygon 51 a telecentric scan lens 52, a transparent sample 54, a stage 55, a focusing lens 56, an aperture 57, and a detector 59. A radiation source irradiates the rotating polygon 51 which directs a moving source beam with varying angular direction onto telecentric scan lens 52. Telecentric scan lens 52 redirects the source beam with varying angular direction to an angle substantially normal to transparent sample 54. As shown in FIG. 7, the source beam causes a scattered radiation to be radiated from transparent sample 54 and stage 55. Scattered radiation from stage 55 occurs due to the transparency of transparent sample 54. A portion of scanning beam 53 passes through transparent sample 54 and illuminates stage 55. Stage 55 is any surface located below transparent sample 54. In many examples there is an air gap between the bottom surface of the transparent sample and the stage. Scattered radiation originating from stage 55 is illustrated in FIG. 7. Focusing lens 56, located at an oblique angle from the plane of incidence of the source beam, receives a portion of the scattered radiation as shown in FIG. 7. The scattered radiation originating from stage 55 passes through transparent sample 54 and travels to focusing lens 56. The scattered radiation from transparent sample 54 also travels to focusing lens 56. As such, both scattered radiation from transparent sample 54 and scattered radiation from stage 55 are focused by focusing lens 56 to focal plane 58. At focal plane 58, aperture 57 limits the scattered radiation allowed to pass to scattered radiation detector 59. In this configuration, the scattered radiation measured by scattered radiation detector 59 includes scattered radiation from both the stage 55 and the transparent sample 54. Measured scattered radiation from stage 55 is problematic in that it is desired to measure only the scattered radiation of transparent sample 54 (not the scattered radiation of stage 55). Therefore, there is a need to create a system in which the scattered radiation from the stage 55 is removed before the scattered radiation originating from the transparent sample 54 is measured.

Figure 8:
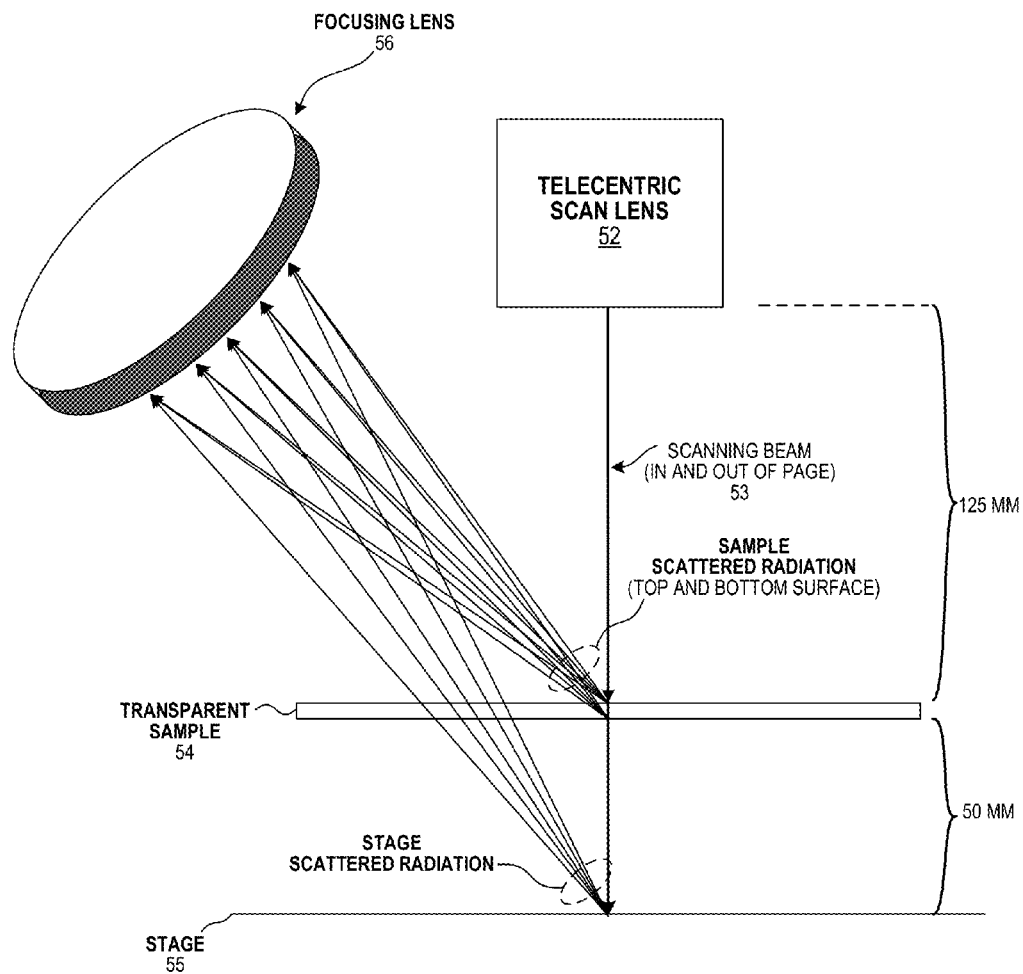
FIG. 8 is an expanded diagram of an optical inspector without a blocker.

FIG. 8 is an expanded diagram of the optical inspector shown in FIG. 7. This expanded view illustrates that scattered radiation originating from the stage 55 may be blocked without blocking the scattered radiation originating from transparent sample 54 by placing a horizontally orientated blocking plane above the transparent sample 54 at a location offset from scanning beam 53.

In one example, the angle of inclination of the focusing lens with respect to the plane of incidence of the scanned beam is approximately forty five degrees.

In one example, the optical inspector also includes a processor. The processor communicates with either detector 59 or a motor controlling the rate of rotation of rotating polygon 51, or both. In one example, detector 59 communicates a signal indicating the intensity of the light detected by detector 59 to the processor. The processor then determines if defects are present in the scanned area of the sample based upon the signal received from detector 59. In another example, the processor sends a signal to a motor controlling the rotating polygon 51. The signal sent to the motor causes the motor to increase or decrease the rate at which the rotating polygon rotates.

Figure 9:
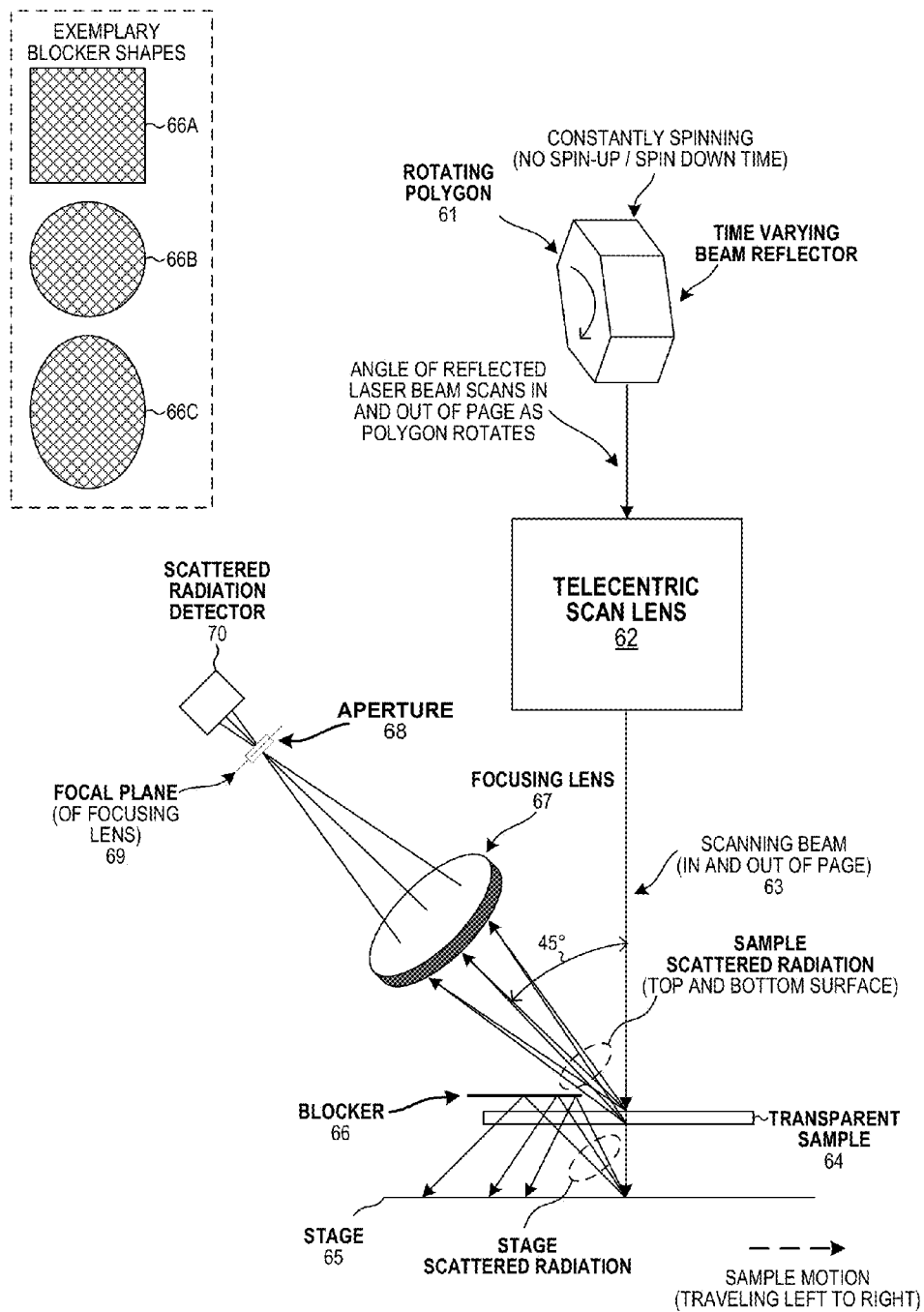
FIG. 9 is a diagram of an optical inspector with a blocker.

FIG. 9 is a diagram of an optical inspector with a blocker of stage scattered radiation. The optical inspector includes a rotating polygon 61 a telecentric scan lens 62, a transparent sample 64, a stage 65, a blocker 66, a focusing lens 67, an aperture 68, and a detector 70. A radiation source irradiates the rotating polygon 61 which directs a moving source beam with varying angular direction onto telecentric scan lens 62. Telecentric scan lens 62 redirects the source beam with varying angular direction to an angle substantially normal to transparent sample 64. As shown in FIG. 9, the source beam causes a scattered radiation to be radiated from transparent sample 64 and stage 65. Scattered radiation from stage 65 occurs due to the transparency of transparent sample 64. A portion of scanning beam 63 passes through transparent sample 64 and illuminates stage 65. Stage 65 is a surface located below transparent sample 64. Scattered radiation originating from stage 65 is illustrated in FIG. 9. Focusing lens 67, located at an oblique angle from the plane of incidence of the source beam, receives a portion of the scattered radiation originating from the transparent sample 64 as shown in FIG. 9. The scattered radiation originating from stage 65 passes through transparent sample 64 and travels to blocker 66 (not focusing lens 67). Blocker 66 is opaque and either absorbs or redirects scattered radiation originating from stage 65 away from focusing lens 67. As such, only scattered radiation from transparent sample 64 is focused by focusing lens 67 to focal plane 69. At focal plane 69, aperture 68 limits the scattered radiation allowed to pass to scattered radiation detector 70. In this configuration, the scattered radiation measured by scattered radiation detector 70 includes only scattered radiation from the transparent sample 64. Therefore, blocker 66 allows the measurement of scattered radiation originating from transparent sample 64 without contamination of scattered radiation from stage 65.

In one example, blocker 66 is rectangular and opaque like the exemplary blocker labeled 66A. Blocker 66 is fixed in position with respect to the telecentric scan lens 62 and does not move during the scanning of the sample. The scattered radiation originating from the transparent sample 64 is not blocked by blocker 66.

Blocker 66 may be implemented in other non-rectangular shapes, such as circularly shaped blocker 66B, or an epileptically shaped blocker 66C.

The scattered radiation originating from the transparent sample 64 includes scattered radiation from both the top surface and bottom surface of the transparent sample 64. Therefore, the scattered radiation measured by scattered radiation detector 70 includes the scattered radiation from both the top surface and bottom surface of the transparent sample 64.

Figure 10:
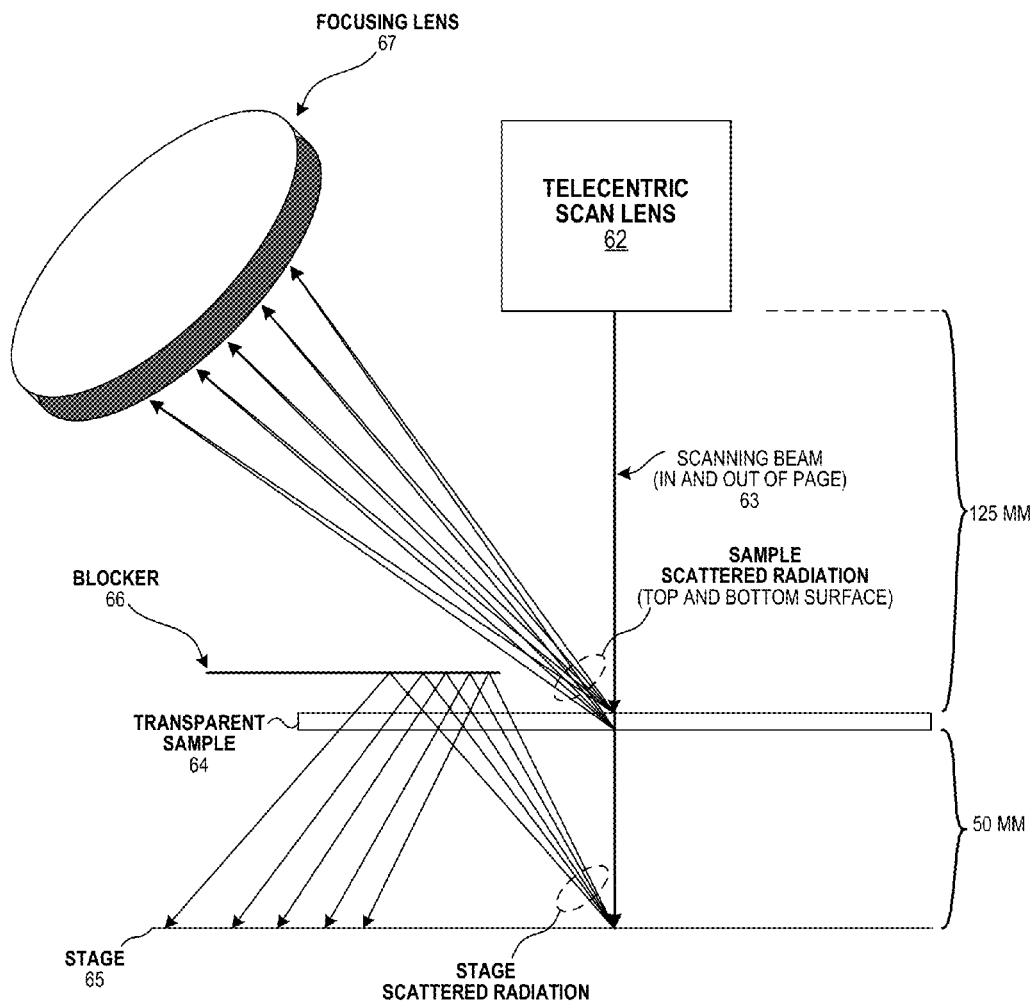
FIG. 10 is an expanded diagram of an optical inspector with a blocker.

FIG. 10 is an expanded diagram of the optical inspector shown in FIG. 9. This expanded view illustrates that scattered radiation originating from the stage 55 may be blocked without blocking the scattered radiation originating from transparent sample 54 by placing a horizontally orientated blocking plane above the transparent sample 54 at a location offset from scanning beam 53.

Figure 11:
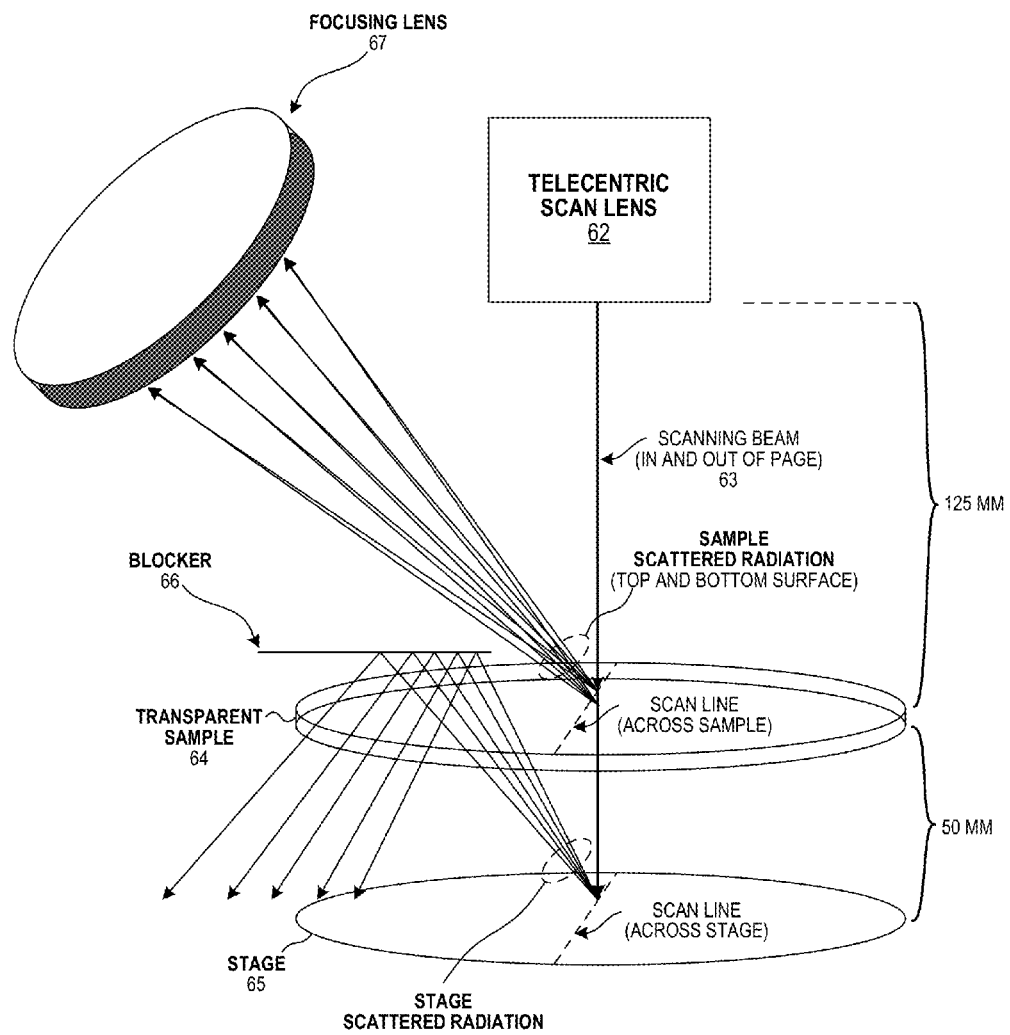
FIG. 11 is an expanded three dimensional diagram of an optical inspector with a blocker.

FIG. 11 is an expanded three-dimensional view of the optical inspector shown in FIG. 9. This three-dimensional view illustrates the scan line generated by telecentric scan lens across the surface of the transparent sample 64 and the stage 65.

In one example, the angle of inclination of the focusing lens 67 with respect to the plane of incidence of the scanned beam is approximately forty five degrees.

In one example, the optical inspector also includes a processor. The processor communicates with either detector 70 or a motor controlling the rate of rotation of rotating polygon 61, or both. In one example, detector 70 communicates a signal indicating the intensity of the light detected by detector 70 to the processor. The processor then determines if defects are present in the scanned area of the sample based upon the signal received from detector 70. In another example, the processor sends a signal to a motor controlling the rotating polygon 61. The signal sent to the motor causes the motor to increase or decrease the rate at which the rotating polygon rotates.

Figure 12:
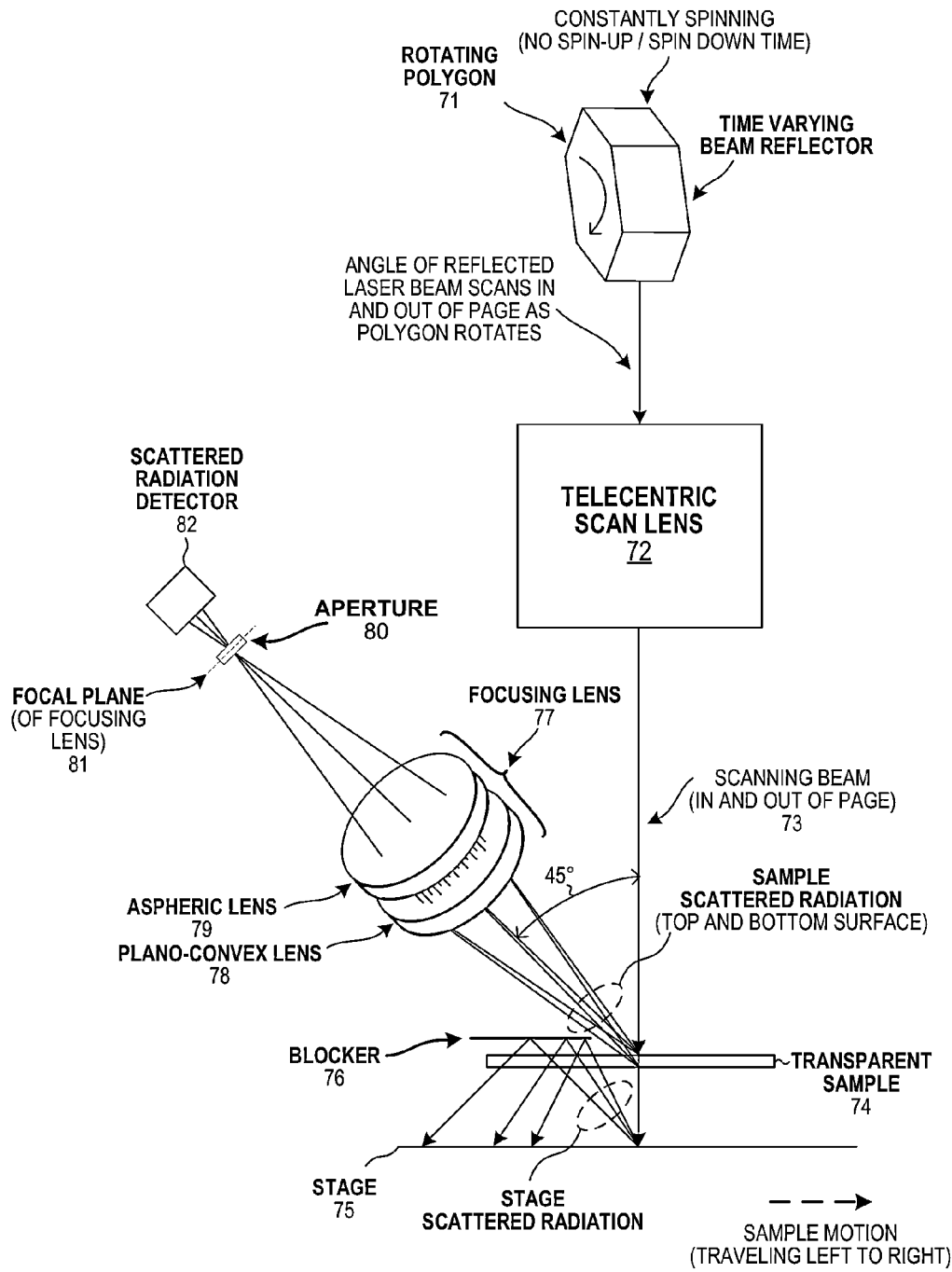
FIG. 12 is a diagram of an optical inspector with a blocker, wherein the focusing lens comprises an aspheric lens and a plano-convex lens.

FIG. 12 is a diagram of an optical inspector with a blocker of stage scattered radiation. The optical inspector includes a rotating polygon 71 a telecentric scan lens 72, a transparent sample 74, a stage 75, a blocker 76, a focusing lens 77, an aperture 80, and a detector 82. A radiation source irradiates the rotating polygon 71 which directs a moving source beam with varying angular direction onto telecentric scan lens 72. Telecentric scan lens 72 redirects the source beam with varying angular direction to an angle substantially normal to transparent sample 74. As shown in FIG. 12, the source beam causes a scattered radiation to be radiated from transparent sample 74 and stage 75. Scattered radiation from stage 75 occurs due to the transparency of transparent sample 74. A portion of scanning beam 73 passes through transparent sample 74 and illuminates stage 75. Stage 75 is a surface located below transparent sample 74. Scattered radiation originating from stage 75 is illustrated in FIG. 12. Focusing lens 77, located at an oblique angle from the plane of incidence of the source beam, receives a portion of the scattered radiation originating from the transparent sample 74 as shown in FIG. 12. Focusing lens 77 includes a pair of lens: an aspheric lens 79 and a plano-convex lens 78. This combination of lenses offers the maximum collection efficiency together with the minimum amount of vignetting. The scattered radiation originating from stage 75 passes through transparent sample 74 and travels to blocker 76 (not focusing lens 77). Blocker 76 is opaque and redirects scattered radiation originating from stage 75 away from focusing lens 77. As such, only scattered radiation from transparent sample 74 is focused by focusing lens 77 to focal plane 81. At focal plane 81, aperture 80 limits the scattered radiation allowed to pass to scattered radiation detector 82. In this configuration, the scattered radiation measured by scattered radiation detector 82 includes only scattered radiation from the transparent sample 74. Therefore, blocker 76 allows the measurement of scattered radiation originating from transparent sample 74 without contamination of scattered radiation from stage 75.

In one example, blocker 76 is rectangular and opaque. Blocker 76 is fixed in position with respect to the telecentric scan lens 72 such that scattered radiation originating from the transparent sample 74 is not blocked by blocker 76.

The scattered radiation originating from the transparent sample 74 includes scattered radiation from both the top surface and bottom surface of the transparent sample 74. Therefore, the scattered radiation measured by scattered radiation detector 82 includes the scattered radiation from both the top surface and bottom surface of the transparent sample 74.

In one example, the angle of inclination of the focusing lens with respect to the plane of incidence of the scanned beam is approximately forty five degrees. In one example, the optical inspector also includes a processor. The processor communicates with either detector 82 or a motor controlling the rate of rotation of rotating polygon 71, or both. In one example, detector 82 communicates a signal indicating the intensity of the light detected by detector 82 to the processor. The processor then determines if defects are present in the scanned area of the sample based upon the signal received from detector 82. In another example, the processor sends a signal to a motor controlling the rotating polygon 71. The signal sent to the motor causes the motor to increase or decrease the rate at which the rotating polygon rotates.

Figure 13:
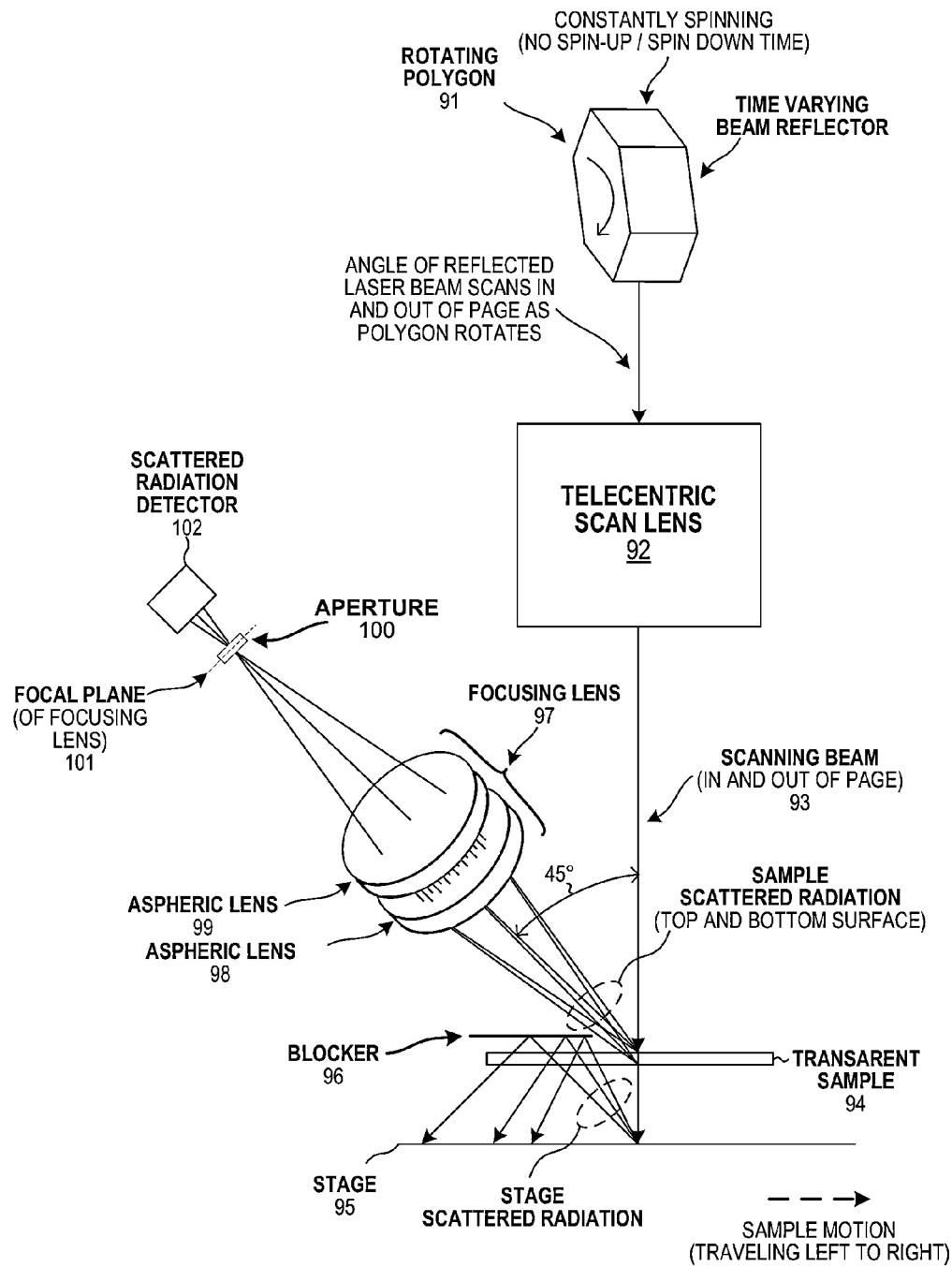
FIG. 13 is a diagram of an optical inspector with a blocker, wherein the focusing lens comprises a first and second aspheric lens.

FIG. 13 is a diagram of an optical inspector with a blocker of stage scattered radiation. The optical inspector includes a rotating polygon 91 a telecentric scan lens 92, a transparent sample 94, a stage 95, a blocker 96, a focusing lens 97, an aperture 100, and a detector 102. A radiation source irradiates the rotating polygon 91 which directs a moving source beam with varying angular direction onto telecentric scan lens 92. Telecentric scan lens 92 redirects the source beam with varying angular direction to an angle substantially normal to transparent sample 94. As shown in FIG. 13, the source beam causes a scattered radiation to be radiated from transparent sample 94 and stage 95. Scattered radiation from stage 95 occurs due to the transparency of transparent sample 94. A portion of scanning beam 93 passes through transparent sample 94 and illuminates stage 95. Stage 95 is a surface located below transparent sample 94. Scattered radiation originating from stage 95 is illustrated in FIG. 13. Focusing lens 97, located at an oblique angle from the plane of incidence of the source beam, receives a portion of the scattered radiation originating from the transparent sample 94 as shown in FIG. 13. Focusing lens 97 includes a pair of lens: a first aspheric lens 98 and a second aspheric lens 99. The benefit of this lens combination is that it offers good collection efficiency together with low vignetting. The scattered radiation originating from stage 95 passes through transparent sample 94 and travels to blocker 96 (not focusing lens 97). Blocker 96 is opaque and redirects scattered radiation originating from stage 95 away from focusing lens 97. As such, only scattered radiation from transparent sample 94 is focused by focusing lens 97 to focal plane 101. At focal plane 101, aperture 100 limits the scattered radiation allowed to pass to scattered radiation detector 102. In this configuration, the scattered radiation measured by scattered radiation detector 102 includes only scattered radiation from the transparent sample 94. Therefore, blocker 96 allows the measurement of scattered radiation originating from transparent sample 94 without contamination of scattered radiation from stage 95.

In one example, blocker 96 is rectangular and opaque. Blocker 96 is fixed in position with respect to the telecentric scan lens 92 such that the scattered radiation originating from the transparent sample 94 is not blocked by blocker 96.

The scattered radiation originating from the transparent sample 94 includes scattered radiation from both the top surface and bottom surface of the transparent sample 94. Therefore, the scattered radiation measured by scattered radiation detector 102 includes the scattered radiation from both the top surface and bottom surface of the transparent sample 94.

In one example, the angle of inclination of the focusing lens with respect to the plane of incidence of the scanned beam is approximately forty five degrees. In one example, the optical inspector also includes a processor. The processor communicates with either detector 102 or a motor controlling the rate of rotation of rotating polygon 91, or both. In one example, detector 102 communicates a signal indicating the intensity of the light detected by detector 102 to the processor. The processor then determines if defects are present in the scanned area of the sample based upon the signal received from detector 102. In another example, the processor sends a signal to a motor controlling the rotating polygon 91. The signal sent to the motor causes the motor to increase or decrease the rate at which the rotating polygon rotates.

Figure 14:
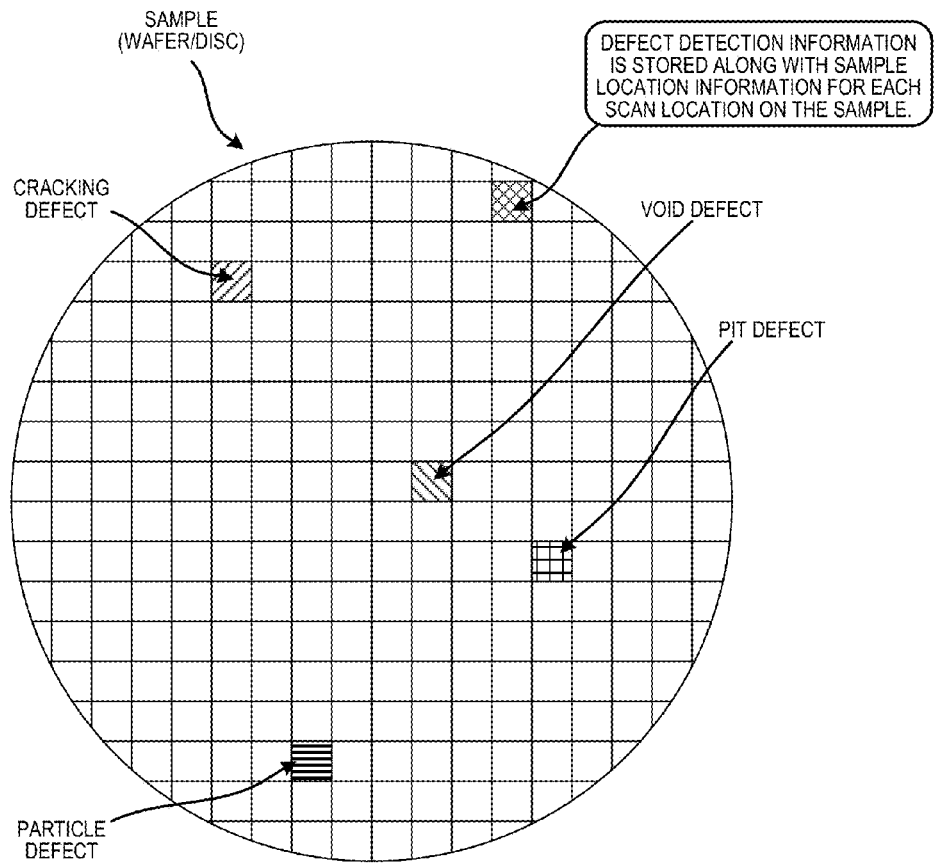
FIG. 14 is a diagram of a sample defect mapping.

FIG. 14 is a diagram of a transparent sample (i.e. wafer or disc) illustrating different scan areas on the surface of the sample. Each scan area is a portion of the sample which is inspected during an optical scan by the optical inspector. The information determined as a result of each optical scan is stored with information location indicating the location on the sample where the optical inspection was performed.

In one example, a processor included in the optical inspector determines whether a defect is present in the current scan location on the sample and records "type of defect information" and the scan location into memory. The type of defect information and scan location information is then read from memory and used to determine which portions of the sample are to be used for production and which portions of the sample are not to be used for production.

In a second example, a processor included in the optical inspector determines various "defect indication information" present in the current scan location on the sample and records the defect indication information (i.e. surface slope, total reflectivity, intensity of scattered radiation and intensity of near specular scattered radiation) and the scan location information into memory. The determination of type of defect information in the associated scan location is then determined at a post processing stage after the optical scan of the current location is completed. The type of defect information and scan location information are used to determine which portions of the sample are to be used for production and which portions of the sample are not to be used for production. Alternatively, type of defect information may be used to control the sample manufacturing process.

It is desirable to determine which surface (top or bottom) of the transparent sample is the originating source of the scattered radiation. This can be accomplished by comparing contemporaneous measurements of scattered radiation and specular reflection of one surface of the transparent sample. In one example, contemporaneous measurements of scattered radiation and top surface specular reflection are compared to determine the originating surface of the measured scattered radiation. This example is illustrated in FIGS. 15, 16, 17, and 19.

Figure 15:
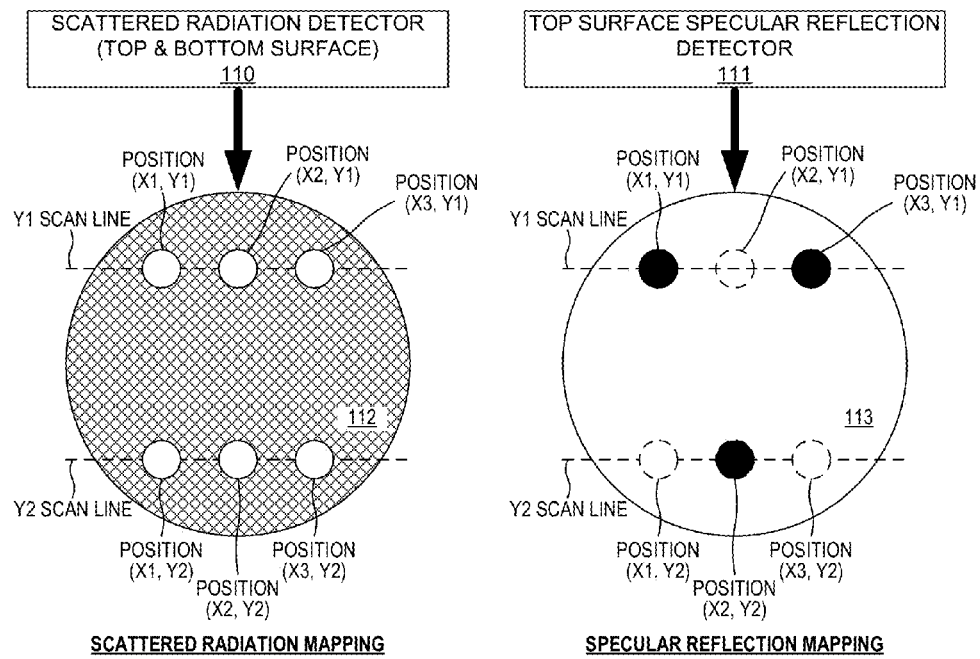
FIG. 15 is a diagram of intensity mapping of scattered light and specular reflection.

FIG. 15 is a diagram of measured scattered radiation and measured specular reflection. Each position labeled on the scattered radiation mapping correlates to the same position similarly labeled on the specular reflection mapping and was contemporaneously measured. Empty position circles indicate measurements above a threshold value. Filled in position circles indicate measurements below a threshold value. Each position represents a measurement taken along a scan line. Measured scattered radiation 112 includes scattered radiation from the top surface and the bottom surface of the transparent sample. Measured specular reflection 113 includes only specular reflection from the top surface of the transparent sample.

Figure 16:
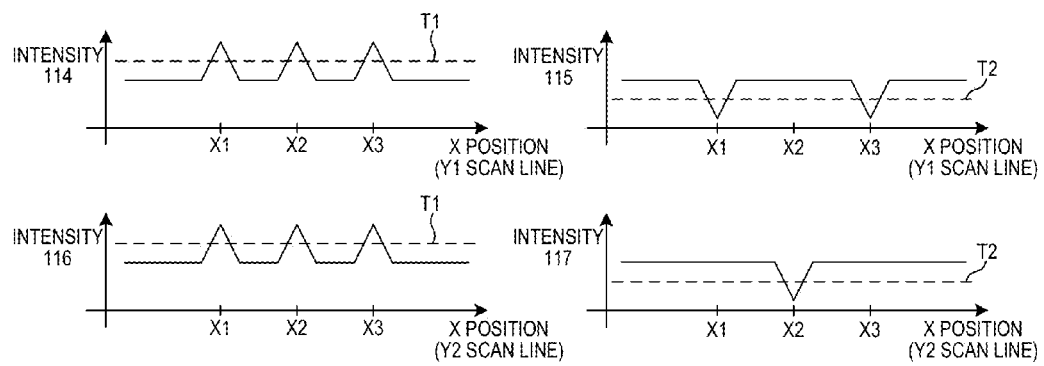
FIG. 16 is a diagram illustrating the relationship between intensity and scan line position.

FIG. 16 is a diagram of measured intensity verses position. FIG. 16 illustrates measured scattered radiation intensity 114 verses position along Y1 scan line, measured scattered radiation intensity 116 verses position along Y2 scan line, measured top surface specular reflection intensity 115 verses position along Y1 scan line, and measured top surface specular reflection intensity 117 verses position along Y2 scan line. Application of threshold values T1 and T2 to the measurements of FIG. 16 generate the measurement circles shown in FIG. 15. For example, when measured intensity 114 is greater than threshold T1 the corresponding circle in FIG. 15 is empty. Similarly, when the measured intensity 115 is below threshold value T2 the corresponding circle in FIG. 15 is filled-in.

FIG. 17 is a table illustrating the logic used to distinguish the source of the scattered radiation based upon the measured intensity of the top surface specular reflection. At a given location (x-y) it is determined if: (i) is the intensity of the scattered radiation greater than threshold value T1, and (ii) is the intensity of the specular reflection of the top surface of the transparent sample less than threshold value T2. If the measured intensity of the scatter radiation is greater than the first threshold value T1 and the measured intensity of the specular reflection is less than the threshold value T2, then the source of the scattered radiation is the top surface of the transparent sample. If the measured intensity of the scatter radiation is greater than the first threshold value T1 and the measured intensity of the specular reflection is greater than the threshold value T2, then the source of the scattered radiation is the bottom surface of the transparent sample. If the intensity of the scattered radiation is less than the threshold value T1, then there is no useful scattered radiation.

Figure 19:
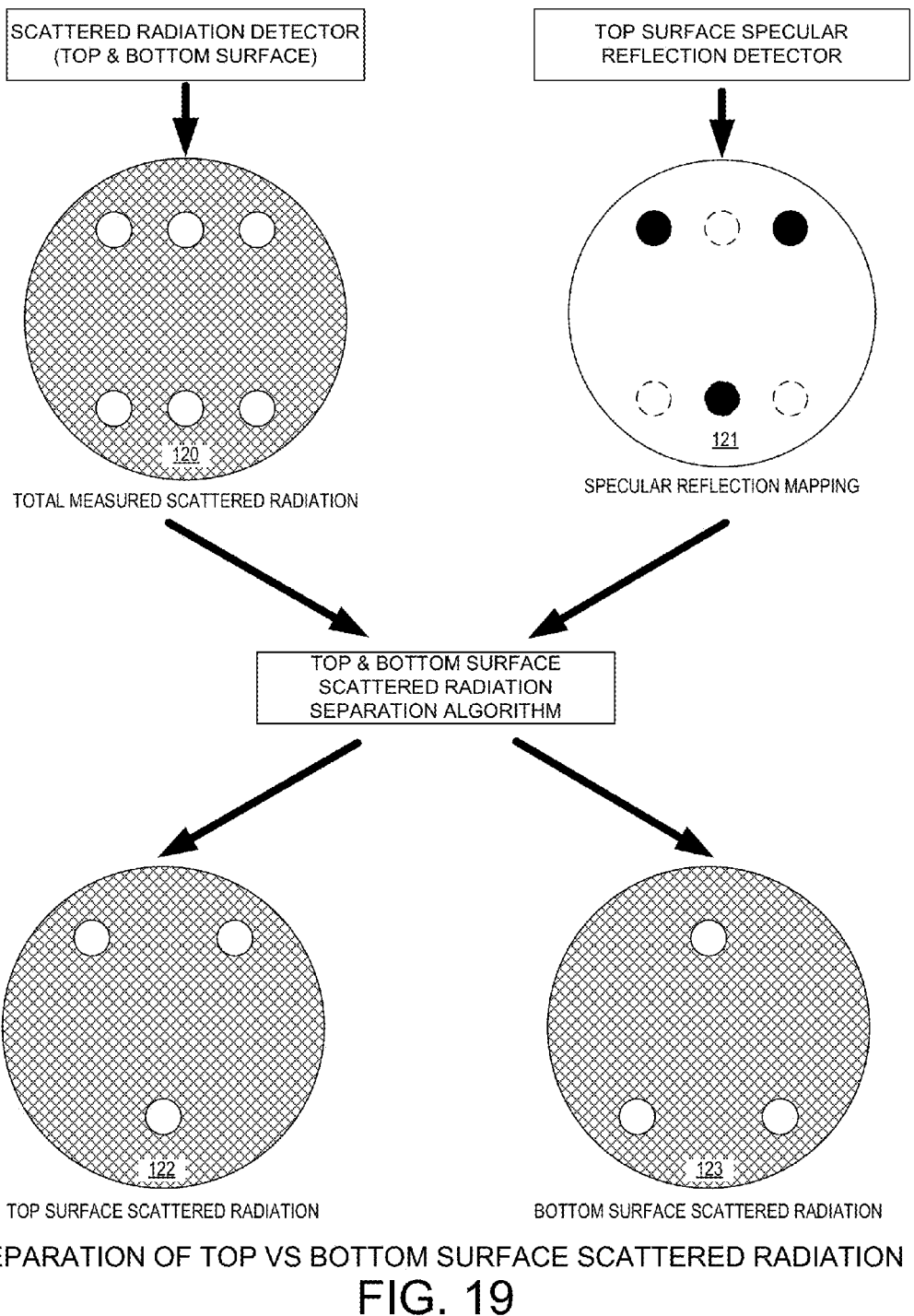
FIG. 19 is a diagram illustrating the separation of the top and bottom surface scattered radiation.

FIG. 19 is a diagram illustrating the process of distinguishing scattered radiation originating from the top surface of the transparent sample from scattered radiation originating from the bottom surface of the transparent sample. Contemporaneously, the scattered radiation detector measures the intensity of the scattered radiation and the top surface specular reflection detector measures the intensity of the specular reflection. The contemporaneous measurements are processed by an algorithm that implements the logic illustrated in the table of FIG. 17. The output of the algorithm then indicates which surface of the transparent sample from which the scattered radiation originated.

The algorithm of FIG. 19 may be implemented by software code executed on a processor. Alternatively, the algorithm of FIG. 19 may be implemented by a state machine, lookup table or any other methodologies well known in the art.

An alternative solution, wherein the specular reflection of the bottom surface of the transparent sample is used to determine the originating surface of the scattered radiation is illustrated in FIG. 18. FIG. 18 is a table illustrating the logic used to distinguish the source of the scattered radiation based upon the measured intensity of the bottom surface specular reflection. At a given location (x-y) it is determined if: (i) is the intensity of the scattered radiation greater than threshold value T1, and (ii) is the intensity of the specular reflection of the bottom surface of the transparent sample less than threshold value T3. If the measured intensity of the scatter radiation is greater than the first threshold value T1 and the measured intensity of the specular reflection is less than the threshold value T3, then the source of the scattered radiation is the bottom surface of the transparent sample. If the measured intensity of the scatter radiation is greater than the first threshold value T1 and the measured intensity of the specular reflection is greater than the threshold value T3, then the source of the scattered radiation is the top surface of the transparent sample. If the intensity of the scattered radiation is less than the threshold value T1, then there is no useful scattered radiation.

Figure 20:
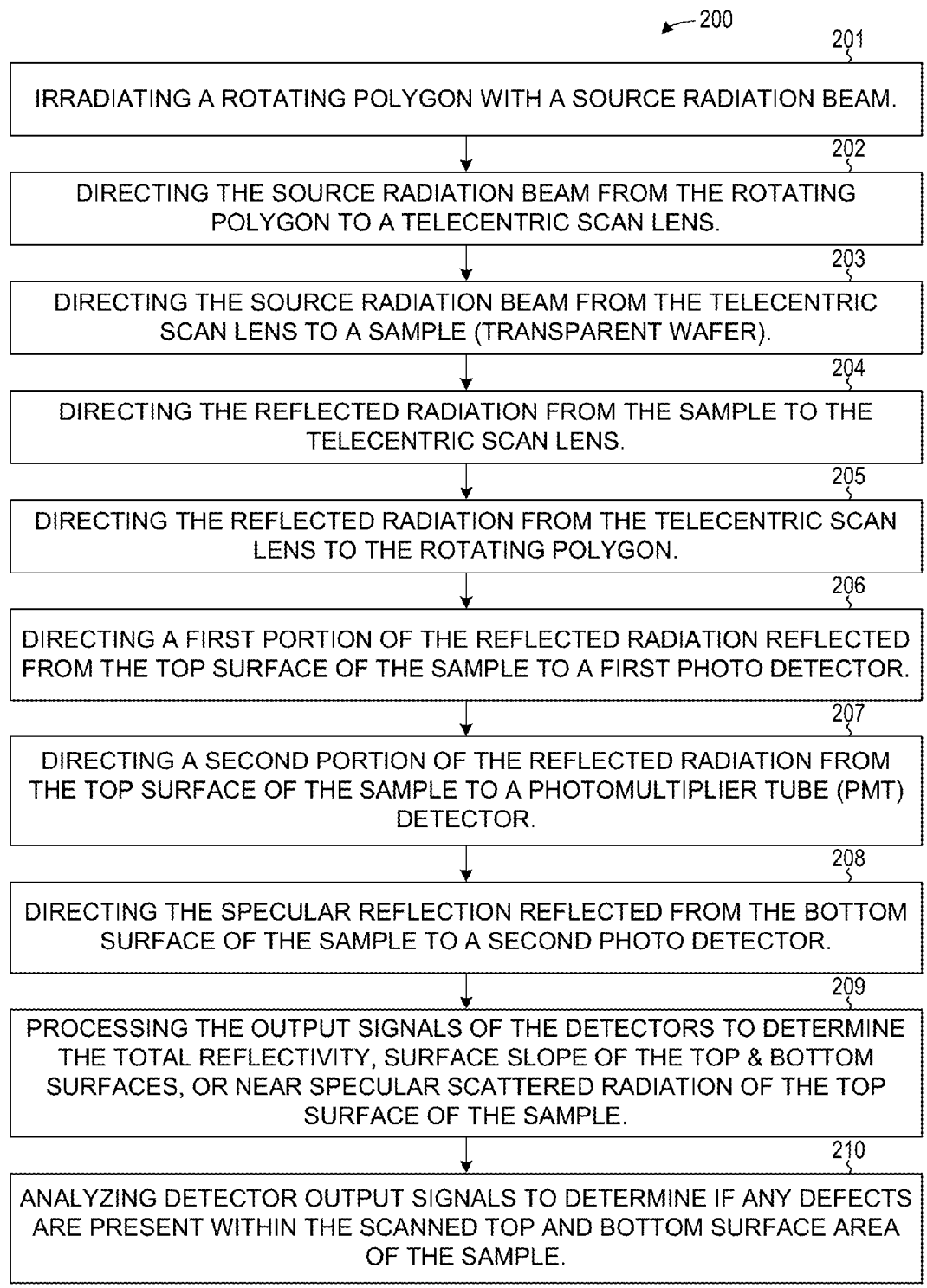
FIG. 20 is a flowchart of steps to determine the total reflectivity, surface slope of top and bottom surfaces, or near specular scattered radiation of the top surface of the sample.

FIG. 20 is a flowchart 200 of steps to perform optical inspection of a transparent sample. In step 201, rotating polygon is irradiated with a source radiation beam. In step 202, the source radiation beam is directed from the rotating polygon to the telecentric scan lens. In step 203, the source radiation beam is directed from the telecentric scan lens to the transparent sample. In step 204, the reflected radiation from the sample is directed to telecentric scan lens. In step 205, the reflected radiation from the telecentric scan lens is directed to the rotating polygon. In step 206, the first portion of the reflected radiation from the top surface of the transparent sample is directed to a first photo-diode detector. In step 207, the second portion of the reflected radiation from the top surface of the transparent sample is directed to photomultiplier tube. In step 208, the reflected radiation from the bottom surface of the transparent sample is directed to the second photo-diode detector. In step 209, the output signals of the detectors are processed to determine the total reflectivity and surface slope of the top and bottom surfaces of the transparent sample, and the near specular scattered radiation of the top surface of the transparent sample.

Figure 21:
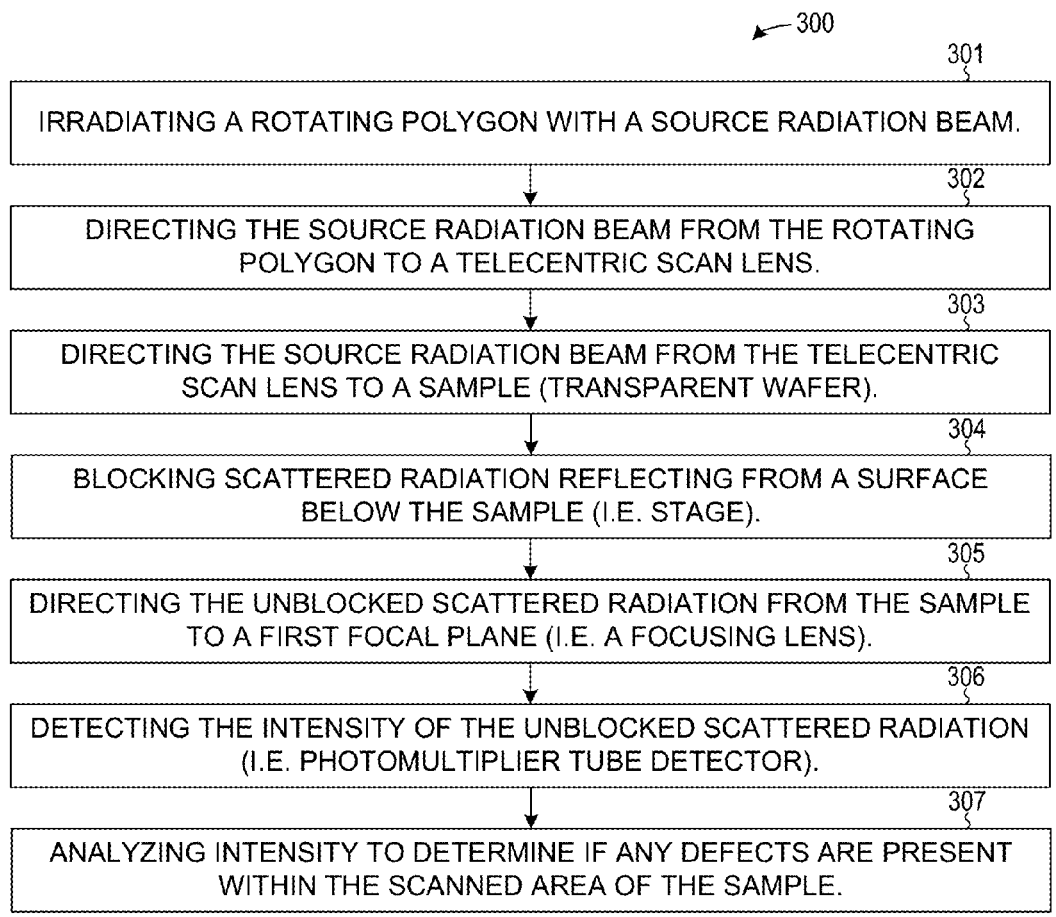
FIG. 21 is a flowchart of steps to detect the intensity of the scattered radiation radiated from the sample.

FIG. 21 is a flowchart 300 of steps to perform optical inspection of a transparent sample. In step 301, rotating polygon is irradiated with a source radiation beam. In step 302, the source radiation beam is directed from the rotating polygon to the telecentric scan lens. In step 303, the source radiation beam is directed from the telecentric scan lens to the transparent sample. In step 304, the scattered radiation reflected from a surface below the transparent sample is blocked. In step 305, the unblocked scattered radiation from the transparent sample is directed to a first focal plane. In step 306, the intensity of the unblocked scattered radiation is detected. In step 307, the intensity is analyzed to determine if any defects are present within the scanned area of the transparent sample.

Figure 22:
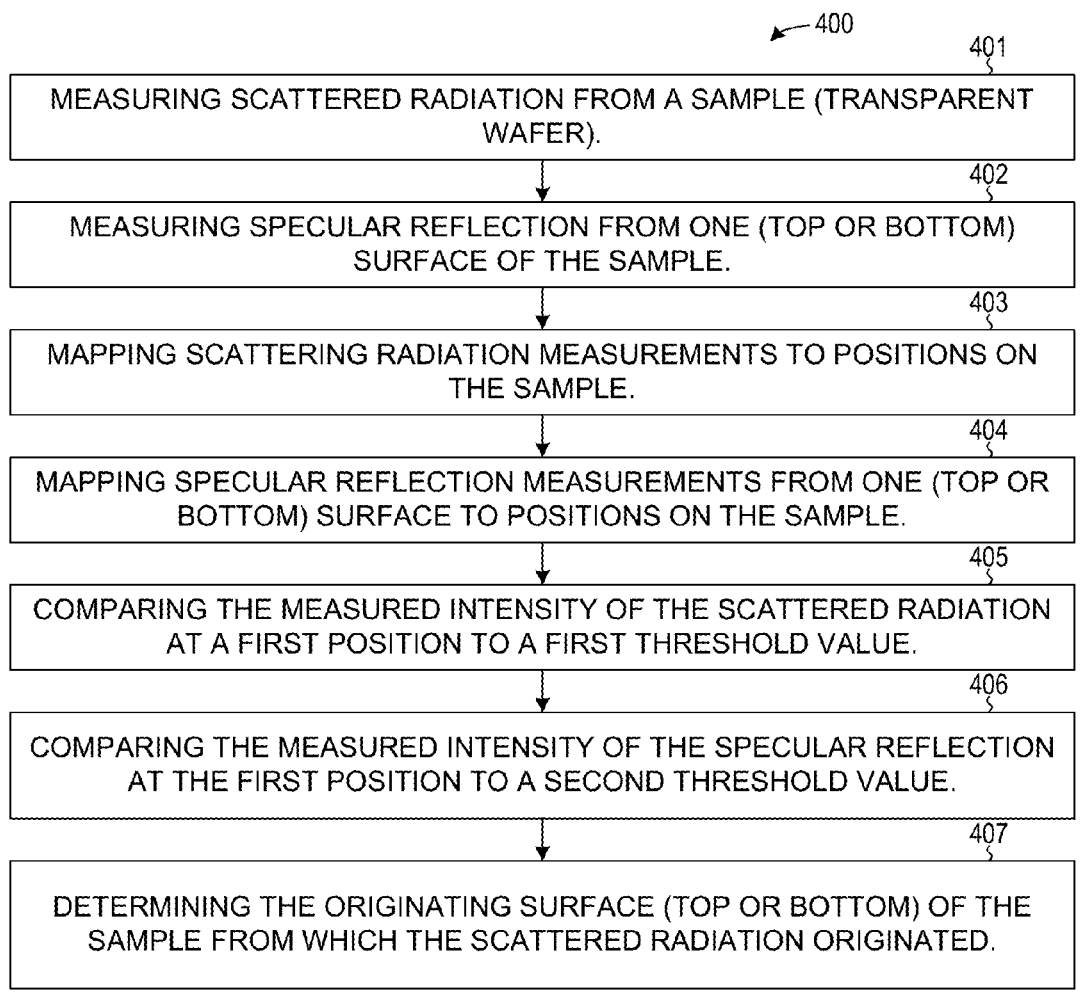
FIG. 22 is a flowchart of steps to determine the surface of the sample from which the scattered radiation originated.

FIG. 22 is a flowchart 400 of steps to perform optical inspection of a transparent sample. In step 401, the scattered radiation from the transparent sample is measured. In step 402, the specular reflection from one surface of the transparent sample is measured. In step 403, the scattered radiation measurement is mapped to a position on the sample. In step 404, the specular reflection measurement is mapped to a position on the transparent sample. In step 405, the measured intensity of the scattered radiation at the first position is compared to the first threshold value. In step 406, the measured intensity of the specular reflection at the first position is compared to the second threshold value. In step 407, the originating surface of the scattered radiation is determined.

Although certain specific embodiments are described above for instructional purposes, the teachings of this patent document have general applicability and are not limited to the specific embodiments described above. Accordingly, various modifications, adaptations, and combinations of various features of the described embodiments can be practiced without departing from the scope of the invention as set forth in the claims.

What is claimed is:

1. An apparatus, comprising:
   a time varying beam reflector;
   a radiating source that irradiates the time varying beam reflector at a first position;
   a first waveplate, wherein the first waveplate is positioned along a source radiation path between the radiating source and the time varying beam reflector;
   a telecentric scan lens that directs source radiation reflected by the time varying beam reflector onto a transparent sample and a stage, wherein the telecentric scan lens directs specular reflected radiation from the transparent sample to the time varying beam reflector at a second position symmetrically opposite the first position about a central axis of the telecentric scan lens, and wherein the irradiation of the transparent sample and the stage causes scattered radiation reflecting from the transparent sample and the stage;
   a beam splitter that receives specular reflected radiation from the time varying beam reflector;
   a second waveplate, wherein the second waveplate is positioned along a reflected radiation path between the time varying beam reflector and the beam splitter;
   a first detector that receives a first portion of the specular reflected radiation from the beam splitter;
   a focusing lens that receives the scattered radiation from the transparent sample;
   a blocker that redirects the scattered radiation from the stage away from the focusing lens, wherein the blocker is located between the focusing lens and an irradiated location on the stage; and
   a second detector located near the focal plane of the focusing lens, wherein a first surface of the transparent sample faces the telecentric scan lens, and wherein a second surface of the transparent sample does not face the telecentric scan lens.

2. The apparatus of claim 1, wherein the specular reflected radiation
   includes: (i) reflected radiation from a first surface of the transparent sample, and (ii) reflected radiation from a second surface of the transparent sample, wherein the polarizing beam splitter redirects a majority of the reflected radiation from the first surface of the transparent sample, and wherein the polarizing beam splitter does not redirect a majority of the reflected radiation from the second surface of the transparent sample.

3. The apparatus of claim 1, further comprising:
   a processor; and
   a memory, wherein the processor receives information from the first and second detectors and stores associated data in the memory.

4. The apparatus of claim 1, further comprising:
   a processor that processes information received from the first and second detectors to determine the surface of the transparent sample from which the scattered radiation originated.

5. The apparatus of claim 1, wherein the first detector is a photodiode bi-cell device, and wherein the second detector is a photomultiplier tube.

6. The apparatus of claim 1, wherein the time varying beam reflector is a rotating polygon, wherein the radiating source is a laser, and wherein the beam splitter is a polarizing beam splitter.

7. The apparatus of claim 1, wherein the first waveplate circularly polarizes the source radiation before the transparent sample is irradiated, and wherein the second waveplate linearly polarizes the specular reflected radiation from the transparent sample.

8. The apparatus of claim 1, wherein the specular reflected radiation that is reflected from the first surface of the transparent sample is shifted in phase by approximately pi radians, wherein the reflected radiation that is reflected from the second surface of the transparent sample is shifted in phase by approximately zero radians, wherein the second waveplate vertically polarizes the specular reflected radiation from the first surface of the transparent sample, wherein the second waveplate horizontally polarizes the specular reflected radiation from the second surface of the transparent sample, and wherein the beam splitter only reflects vertically polarized radiation.

9. A method, comprising:
(a) irradiating a transparent sample;
(b) measuring specular reflection from a first surface of the transparent sample;
(c) measuring scattered radiation from the transparent sample, wherein the measuring of (c) further comprises:
(d) blocking scattered radiation from a stage while not blocking scattered radiation from the transparent sample;
(e) focusing scattered radiation from the transparent sample to a focal plane of the focusing lens; and
(f) detecting intensity of the focused scattered radiation from the transparent sample; and
(g) determining a surface of the transparent sample from which the scattered radiation originated, wherein the determining of (g) further comprises:
(h) determining if the measured scattered radiation from the transparent sample is greater than a first threshold value; and
(i) determining if the specular reflection from a first surface of the transparent sample is less than a second threshold value, wherein the first surface of the transparent sample is irradiated before a second surface of the transparent sample.

10. The method of claim 9, wherein the irradiating of (a) further comprises:
(a1) irradiating a first position on a time varying beam reflector with a source radiation beam; and
(a2) directing the source radiation beam from the time varying beam reflector to a telecentric scan lens, thereby directing a scanning beam onto the transparent sample and a stage.

11. The method of claim 10, wherein the irradiating of (a1) is performed by a laser, and wherein the time varying beam reflector is a rotating polygon.

12. The method of claim 9, wherein the measuring of (b) further comprises:
(b1) directing reflected radiation onto the time varying beam reflector to produce a stationary reflected beam; and (b2) directing a first portion of the stationary reflected beam onto a first detector.

13. The method of claim 12, wherein the directing of (b1) is performed by a telecentric scan lens, and wherein the directing of (b2) is performed by a polarizing beam splitter.

14. The method of claim 9, wherein the blocking of (c1) is performed by a blocker, wherein the focusing of (e) is performed by a focusing lens, and wherein the detecting of (f) is performed by a photomultiplier tube.

15. The method of claim 9, wherein the determining of (h) and (i) are performed by a processor, wherein the processor communicates with a memory containing information representing the measured scattered radiation, the measured specular reflection, the first threshold value, and the second threshold value.

16. The method of claim 9, wherein the measured scattered radiation from the transparent sample is greater than a first threshold value, wherein the specular reflection from a first surface of the transparent sample is less than a second threshold value, and wherein the surface of the transparent sample from which the scattered radiation originated is the top surface of the transparent sample.

17. The method of claim 9, wherein the measured scattered radiation from the transparent sample is greater than a first threshold value, wherein the specular reflection from a first surface of the transparent sample is greater than or equal to a second threshold value, and wherein the surface of the transparent sample from which the scattered radiation originated is the bottom surface of the transparent sample.

18. An apparatus, comprising:
a time varying beam reflector;
a radiating source that irradiates the time varying beam reflector at a first position;
a telecentric scan lens that directs source radiation reflected by the time varying beam reflector onto a transparent sample and a stage, wherein the telecentric scan lens directs specular reflected radiation from the transparent sample to the time varying beam reflector at a second position symmetrically opposite the first position about a central axis of the telecentric scan lens, and wherein the irradiation of the transparent sample and the stage causes scattered radiation reflecting from the transparent sample and the stage; and
means for measuring specular reflection from a first surface of a transparent sample, for blocking scattered radiation from the stage while not blocking scattered radiation from the transparent sample for measuring scattered radiation from the transparent sample, and for determining the surface of the transparent sample from which the scattered radiation originated.

19. The apparatus of claim 18, wherein the means include a first detector, a second detector, a first waveplate, a second waveplate, a blocker, and a polarizing beam splitter.

* * * * *